(12) United States Patent
Grossniklaus et al.

(10) Patent No.: US 6,239,327 B1
(45) Date of Patent: May 29, 2001

(54) SEED SPECIFIC POLYCOMB GROUP GENE AND METHODS OF USE FOR SAME

(75) Inventors: Ueli Grossniklaus, Cold Spring Harbor; Jean-Philippe Vielle-Calzada, Huntington, both of NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 09/061,769

(22) Filed: Apr. 16, 1998

(51) Int. Cl.$^7$ ............................... A01H 5/00; A01H 5/10; C12N 15/82; C12N 15/83; C12N 5/04

(52) U.S. Cl. ........................ 800/278; 800/284; 800/290; 800/295; 800/298; 536/23.1; 536/23.6; 435/6; 435/69.1; 435/468; 435/419; 435/320.1; 435/252.3

(58) Field of Search ................................... 536/23.6, 23.1; 800/303, 278, 284, 290, 295, 298; 435/6, 252.3, 69.1, 468, 419, 320.1

(56) References Cited

U.S. PATENT DOCUMENTS

| | | | |
|---|---|---|---|
| 5,686,649 | 11/1997 | Chua | 800/285 |
| 5,710,367 | 1/1998 | Kindiger | 800/266 |

FOREIGN PATENT DOCUMENTS

| | | | |
|---|---|---|---|
| WO 96/04393 | 2/1996 | (WO) | C12N/15/82 |
| WO 96/35784 | 11/1996 | (WO) | C12N/15/12 |
| WO 97/10704 | 3/1997 | (WO) | A01H/5/00 |

OTHER PUBLICATIONS

Napoli et al. The Plant Cell. 1989. vol. 2: 278–289.*
Spencer et al. 1992. Plant Molecular Biology. 1992. vol. 18: 201–210.*
Chaudhury, A.M., et al., "Fertilization–Independent Seed Development in Arabidopsis Thaliana", *Proceedings of the National Academy of Sciences of the U.S.A.*, vol. 94:4223–4228 (1997) Abstract XP002111700.
Goodrich. J., et al., "A Polycomb–Group Gene Regulates Homeotic Gene Expression in Arabidopsis", *Nature*, vol. 386:44–51 (1997) Abstract XP002111701.
Grossniklaus, U., et al., "Maternal Control of Embryogenesis by MEDEA, a Poly comb Group Gene in Arabidopsis", *Science*, vol. 280:446–450 (1998) XP002111702.
Luo, M., et al., "Genes Controlling Fertilization–Independent Seed Development in Arabidopsis Thaliana", *Proceedings of the National Academy of Sciences of the U.S.A.*, vol. 96:296–301 (1999) XP002111703.
Kiyosue, T., et al., "Control of Fertilization–Independent Endosperm Development by the MEDEA Polycomb Gene In Arabidopsis", *Proceedings of the National Academy of Sciences of the U.S.A.*, vol. 96:4186–4191 (1999) XP002111704.

Ohad, N., et al., "Mutations in FIE, a WD Polycomb Group Gene, Allow Endosperm Development Without Fertilization", *The Plant Cell*, vol. 11:407–415 (1999) XP002111705.
Goodrich, J., "Plant Development: MEDEA's Maternal Instinct", *Current Biology*, vol. 8(14):R480–484 (1998) XP002112376.
Pruess, D., "Chromatin Silencing and Arabidopsis Development: A Role for Polycomb Proteins", *The Plant Cell*, vol. 11:765–767 (1999) XP002111706.
E.A. Carrington, et al., "The *Drosophila Enhancer of zeste* gene encodes a chromosomal protein: examination of wild–type and mutant protein distribution", Development, vol. 122, 4073–4083 (1996).
O. Hobert, et al., "Interaction of Vav with ENX–1, a Putative Transcriptional Regulator of Homeobox Gene Expression", *Mol. Cell. Biol.* 16, 3066–3073 (1996).
Jones, R.S. et al., "The *Drosophila* Polycomb–Group Gene *Enhancer of zeste* Contains a Region with Sequence Similarity to *Trithorax*", *Mol. Cell. Biol.* 13, 6357–6388 (1993).
M.D. Phillips, et al., "Mutations in *Polycombeotic*, a Drosophila Polycomb–Group Gene, Cause a Wide Range of Maternal and Zygotic Phenotypes", *Genetics*, vol. 125, 91–101 (1990).
A.M. Mazo, et al, "The trithorax gene, a trans–accting regulator of the bithorax complex in *Drosophila*, encodes a protein with zinc–binding domains", *Proc. Natl. Acad. Sci. USA* 87, 2112–2116 (1990).
Simon, J., "Locking in stable states of gene expression: transcriptional control during *Drosophila* development", *Curr Opin. Cell Biol.* vol. 7, 376–385 (1995).
LaJeunesse, D., et al., "E(z) : a polycomb group gene or a trithorax group gene?", Development, vol. 122, 2189–2197 (1996).
Goodrich, J., et al., "A Polycomb–group gene regulates homeotic gene expression in *Arabidopsis*", Nature 386, 44–51 (1997).
D.C. Tkachuk, et al., "Involvement of a Homolog of *Drosophila Trithorax* by 11q23 Chromosomal Translocations in Acute Leukemias", *Cell* 71, 691 (1992.
Gu, Y., et al., "The t(4;11) Chromosome Translocation of Human Acute Leukemias Fuses the ALL–1 Gene, Related to *Drosophila trithorax*, to the AF–4 Gene", *Cell*, vol. 71, 701–708 (1992).

* cited by examiner

Primary Examiner—David T. Fox
Assistant Examiner—Ousama Zaghmout
(74) Attorney, Agent, or Firm—Zarley, McKee, Thomte, Voorhees & Sease

(57) ABSTRACT

This invention relates to the isolation and characterization of a Polycomb gene from Arabidopsis with maternal control of embryogenesis. The novel gene and gene product may be used to manipulate embryo and endosperm cell proliferation for the generation of parthenocarpy, seed specific characteristics, inhibition of propagation of undesirable plants or apomixis in Arabidopsis and other plant types. Two mutations of this gene have also been identified which identify maternal effect embryo lethality.

17 Claims, 4 Drawing Sheets

(3 of 4 Drawing Sheet(s) Filed in Color)

```
AGGCGAGTGGTTAATGGAGAAGGAAAACCATGAGGACGATGGTGAGGGTTT
GCCACCCGAACTAAATCAGATAAAAGAGCAAATCGAAAAGGAGAGATTTCT
GCATATCAAGAGAAAATTCGAGCTGAGATACATTCCAAGTGTGGCTACTCAT
GCTTCACACCATCAATCGTTTGACTTAAACCAGCCCGCTGCAGAGGATGATA
ATGGAGGAGACAACAAATCACTTTTGTCGAGAATGCAAAACCCACTTCGTCA
TTTCAGTGCCTCATCTGATTATAATTCTTACGAAGATCAAGGTTATGTTCTTG
ATGAGGATCAAGATTATGCTCTTGAAGAAGATGTACCATTATTTCTTGATGAA
GATGTACCATTATTACCAAGTGTCAAGCTTCCAATTGTTGAGAAGCTACCACG
ATCCATTACATGGGTCTTCACCAAAAGTAGCCAGCTGATGGCTGAAAGTGAT
TCTGTGATTGGTAAGAGACAAATCTATTATTTGAATGGTGAGGCACTAGAATT
GAGCAGTGAAGAAGATGAGGAAGATGAAGAAGAAGATGAGGAAGAAATCA
AGAAAGAAAAATGCGAATTTTCTGAAGATGTAGACCGATTTATATGGACGGT
TGGGCAGGACTATGGTTTGGATGATCTGGTCGTGCGGCGTGCTCTCGCCAAGT
ACCTCGAAGTGGATGTTTCGGACATATTGGAAAGATACAATGAACTCAAGCT
TAAGAATGATGGAACTGCTGGTGAGGCTTCTGATTTGACATCCAAGACAATA
ACTACTGCTTTCCAGGATTTTGCTGATAGACGTCATTGCCGTCGTTGCATGAT
ATTCGATTGTCATATGCATGAGAAGTATGAGCCCGAGTCTAGATCCAGCGAA
GACAAATCTAGTTTGTTTGAGGATGAAGATAGACAACCATGCAGTGAGCATT
GTTACCTCAAGGTGAGGAGTGTGACAGAAGCTGATCATGTGATGGATAATGA
TAACTCTATATCAAACAAGATTGTGGTCTCAGATCCAAACAACACTATGTGG
ACGCCTGTAGAGAAGGATCTTTACTTGAAAGGAATTGAGATATTTGGGAGAA
ACAGTTGTGATGTTGCATTAAACATACTTCGGGGGCTTAAGACGTGCCTAGA
GATTTACAATTACATGCGCGAACAAGATCAATGTACTATGTCATTAGACCTTA
ACAAAACTACACAAGACACAATCAGGTTACCAAAAAAGTATCTCGAAAAA
GTAGTAGGTCGGTCCGCAAAAAATCGAGACTCCGAAAATATGCTCGTTATCC
GCCTGCTTTAAAGAAAACAACTAGTGGAGAAGCTAAGTTTTATAAGCACTAC
ACACCATGCACTTGCAAGTCAAAATGTGGACAGCAATGCCCTTGTTTAACTC
ACGAAAATTGCTGCGAGAAATATTGCGGGTGCTCAAAGGATTGCAACAATCG
CTTTGGAGGATGTAATTGTGCAATTGGCCAATGCACAAATCGACAATGTCCTT
GTTTTGCTGCTAATCGTGAATGCGATCCAGATCTTTGTCGGAGTTGTCCTCTT
AGCTGTGGAGATGGCACTCTTGGTGAGACACCAGTGCAAATCCAATGCAAGA
ACATGCAATTCCTCCTTCAAACCAATAAAAGATTCTCATTGGAAAGTCTGAT
GTTCATGGATGGGGTGCATTTACATGGACTCTCTTAAAAAGAATGAGTATCT
CGGAGAATATACTGGAGAACTGATCACTCATGATGAAGCTAATGAGCGTGGG
AGAATAGAAGATCGGATTGGTTCTTCCTACCTCTTTACCTTGAATGATCAGCT
CGAAATCGATGCTCGCCGTAAAGGAAACGAGTTCAAATTTCTCAATCACTCA
GCAAGACCTAACTGCTACGCCAAGTTGATGATTGTGAGAGGAGATCAGAGGA
TTGGTCTATTTGCGGAGAGAGCAATCGAAGAAGGTGAGGAGCTTTTCTTCGA
CTACTGCTATGGACCAGAACATGCGGATTGGTCGCGTGGTCGAGAACCTAGA
AAGACTGGTGCTTCTAAAAGGTCTAAGGAAGCCCGTCCAGCTCGTTAGTTTTT
GATCTGAGGAGAAGCAGCAATTCAAGCAGTCCTTTTTTTATGTTATGGTATAT
CAATTAATAATGTAATGCTATTTTGTGTTACTAAACCAAAACTTAAGTTTCTG
TTTTATTTGTTTTAGGGTGTTTTGTTTGTATCATATGTGTCTTAACTTTCAAAGT
TTTCTTTTTGTATTTCAATTTAAAAACAATGTTTATGTTGTTAAAAAAAAAAA
AAAAAAACTCGAG
```

*Fig. 1*

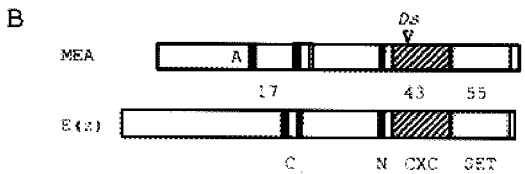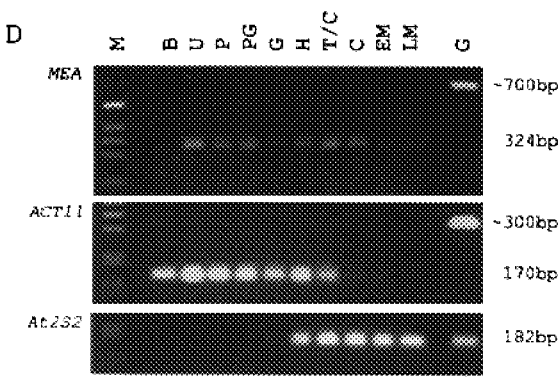
Fig. 4

SEQUENCE LISTING

<160> NUMBER OF SEQ ID NOS: 21

<210> SEQ ID NO 1
<211> LENGTH: 2315
<212> TYPE: DNA
<213> ORGANISM: Artificial Sequence
<220> FEATURE:
<223> OTHER INFORMATION: Description of Artificial Sequence: MEAwt
<221> NAME/KEY: CDS
<222> LOCATION: (14)..(2083)

<400> SEQUENCE: 1

```
aggcgagtgg tta atg gag aag gaa aac cat gag gac gat ggt gag ggt         49
            Met Glu Lys Glu Asn His Glu Asp Asp Gly Glu Gly
              1               5                   10 ttg cca ccc gaa cta aat cag ata aaa gag caa atc gaa aag gag aga        97
Leu Pro Pro Glu Leu Asn Gln Ile Lys Glu Gln Ile Glu Lys Glu Arg
         15                  20                  25 ttt ctg cat atc aag aga aaa ttc gag ctg aga tac att cca agt gtg       145
Phe Leu His Ile Lys Arg Lys Phe Glu Leu Arg Tyr Ile Pro Ser Val
     30                  35                  40 gct act cat gct tca cac cat caa tcg ttt gac tta aac cag ccc gct       193
Ala Thr His Ala Ser His His Gln Ser Phe Asp Leu Asn Gln Pro Ala
 45                  50                  55                  60 gca gag gat gat aat gga gga gac aac aaa tca ctt ttg tcg aga atg       241
Ala Glu Asp Asp Asn Gly Gly Asp Asn Lys Ser Leu Leu Ser Arg Met
                 65                  70                  75 caa aac cca ctt cgt cat ttc agt gcc tca tct gat tat aat tct tac       289
Gln Asn Pro Leu Arg His Phe Ser Ala Ser Ser Asp Tyr Asn Ser Tyr
             80                  85                  90 gaa gat caa ggt tat gtt ctt gat gag gat caa gat tat gct ctt gaa       337
Glu Asp Gln Gly Tyr Val Leu Asp Glu Asp Gln Asp Tyr Ala Leu Glu
         95                  100                 105 gaa gat gta cca tta ttt ctt gat gaa gat gta cca tta tta cca agt       385
Glu Asp Val Pro Leu Phe Leu Asp Glu Asp Val Pro Leu Leu Pro Ser
    110                 115                 120 gtc aag ctt cca att gtt gag aag cta cca cga tcc att aca tgg gtc       433
Val Lys Leu Pro Ile Val Glu Lys Leu Pro Arg Ser Ile Thr Trp Val
125                 130                 135                 140 ttc acc aaa agt agc cag ctg atg gct gaa agt gat tct gtg att ggt       481
Phe Thr Lys Ser Ser Gln Leu Met Ala Glu Ser Asp Ser Val Ile Gly
                145                 150                 155 aag aga caa atc tat tat ttg aat ggt gag gca cta gaa ttg agc agt       529
Lys Arg Gln Ile Tyr Tyr Leu Asn Gly Glu Ala Leu Glu Leu Ser Ser
            160                 165                 170 gaa gaa gat gag gaa gat gaa gaa gaa gat gag gaa gaa atc aag aaa       577
Glu Glu Asp Glu Glu Asp Glu Glu Glu Asp Glu Glu Glu Ile Lys Lys
        175                 180                 185 gaa aaa tgc gaa ttt tct gaa gat gta gac cga ttt ata tgg acg gtt       625
Glu Lys Cys Glu Phe Ser Glu Asp Val Asp Arg Phe Ile Trp Thr Val
    190                 195                 200 ggg cag gac tat ggt ttg gat gat ctg gtc gtg cgg cgt gct ctc gcc       673
Gly Gln Asp Tyr Gly Leu Asp Asp Leu Val Val Arg Arg Ala Leu Ala
205                 210                 215                 220 aag tac ctc gaa gtg gat gtt tcg gac ata ttg gaa aga tac aat gaa       721
Lys Tyr Leu Glu Val Asp Val Ser Asp Ile Leu Glu Arg Tyr Asn Glu
                225                 230                 235 ctc aag ctt aag aat gat gga act gct ggt gag gct tct gat ttg aca       769
Leu Lys Leu Lys Asn Asp Gly Thr Ala Gly Glu Ala Ser Asp Leu Thr
            240                 245                 250
```

```
tcc aag aca ata act act gct ttc cag gat ttt gct gat aga cgt cat      817
Ser Lys Thr Ile Thr Thr Ala Phe Gln Asp Phe Ala Asp Arg Arg His
        255                 260                 265 tgc cgt cgt tgc atg ata ttc gat tgt cat atg cat gag aag tat gag      865
Cys Arg Arg Cys Met Ile Phe Asp Cys His Met His Glu Lys Tyr Glu
    270                 275                 280 ccc gag tct aga tcc agc gaa gac aaa tct agt ttg ttt gag gat gaa      913
Pro Glu Ser Arg Ser Ser Glu Asp Lys Ser Ser Leu Phe Glu Asp Glu
285                 290                 295                 300 gat aga caa cca tgc agt gag cat tgt tac ctc aag gtg agg agt gtg      961
Asp Arg Gln Pro Cys Ser Glu His Cys Tyr Leu Lys Val Arg Ser Val
                305                 310                 315 aca gaa gct gat cat gtg atg gat aat gat aac tct ata tca aac aag     1009
Thr Glu Ala Asp His Val Met Asp Asn Asp Asn Ser Ile Ser Asn Lys
            320                 325                 330 att gtg gtc tca gat cca aac aac act atg tgg acg cct gta gag aag     1057
Ile Val Val Ser Asp Pro Asn Asn Thr Met Trp Thr Pro Val Glu Lys
        335                 340                 345 gat ctt tac ttg aaa gga att gag ata ttt ggg aga aac agt tgt gat     1105
Asp Leu Tyr Leu Lys Gly Ile Glu Ile Phe Gly Arg Asn Ser Cys Asp
    350                 355                 360 gtt gca tta aac ata ctt cgg ggg ctt aag acg tgc cta gag att tac     1153
Val Ala Leu Asn Ile Leu Arg Gly Leu Lys Thr Cys Leu Glu Ile Tyr
365                 370                 375                 380 aat tac atg cgc gaa caa gat caa tgt act atg tca tta gac ctt aac     1201
Asn Tyr Met Arg Glu Gln Asp Gln Cys Thr Met Ser Leu Asp Leu Asn
                385                 390                 395 aaa act aca caa aga cac aat cag gtt acc aaa aaa gta tct cga aaa     1249
Lys Thr Thr Gln Arg His Asn Gln Val Thr Lys Lys Val Ser Arg Lys
            400                 405                 410 agt agt agg tcg gtc cgc aaa aaa tcg aga ctc cga aaa tat gct cgt     1297
Ser Ser Arg Ser Val Arg Lys Lys Ser Arg Leu Arg Lys Tyr Ala Arg
        415                 420                 425 tat ccg cct gct tta aag aaa aca act agt gga gaa gct aag ttt tat     1345
Tyr Pro Pro Ala Leu Lys Lys Thr Thr Ser Gly Glu Ala Lys Phe Tyr
    430                 435                 440 aag cac tac aca cca tgc act tgc aag tca aaa tgt gga cag caa tgc     1393
Lys His Tyr Thr Pro Cys Thr Cys Lys Ser Lys Cys Gly Gln Gln Cys
445                 450                 455                 460 cct tgt tta act cac gaa aat tgc tgc gag aaa tat tgc ggg tgc tca     1441
Pro Cys Leu Thr His Glu Asn Cys Cys Glu Lys Tyr Cys Gly Cys Ser
                465                 470                 475 aag gat tgc aac aat cgc ttt gga gga tgt aat tgt gca att ggc caa     1489
Lys Asp Cys Asn Asn Arg Phe Gly Gly Cys Asn Cys Ala Ile Gly Gln
            480                 485                 490 tgc aca aat cga caa tgt cct tgt ttt gct gct aat cgt gaa tgc gat     1537
Cys Thr Asn Arg Gln Cys Pro Cys Phe Ala Ala Asn Arg Glu Cys Asp
        495                 500                 505 cca gat ctt tgt cgg agt tgt cct ctt agc tgt gga gat ggc act ctt     1585
Pro Asp Leu Cys Arg Ser Cys Pro Leu Ser Cys Gly Asp Gly Thr Leu
    510                 515                 520 ggt gag aca cca gtg caa atc caa tgc aag aac atg caa ttc ctc ctt     1633
Gly Glu Thr Pro Val Gln Ile Gln Cys Lys Asn Met Gln Phe Leu Leu
525                 530                 535                 540 caa acc aat aaa aag att ctc att gga aag tct gat gtt cat gga tgg     1681
Gln Thr Asn Lys Lys Ile Leu Ile Gly Lys Ser Asp Val His Gly Trp
                545                 550                 555 ggt gca ttt aca tgg gac tct ctt aaa aag aat gag tat ctc gga gaa     1729
Gly Ala Phe Thr Trp Asp Ser Leu Lys Lys Asn Glu Tyr Leu Gly Glu
```

-continued

```
                  560                      565                       570
tat  act  gga  gaa  ctg  atc  act  cat  gat  gaa  gct  aat  gag  cgt  ggg  aga    1777
Tyr  Thr  Gly  Glu  Leu  Ile  Thr  His  Asp  Glu  Ala  Asn  Glu  Arg  Gly  Arg
               575                      580                      585 ata  gaa  gat  cgg  att  ggt  tct  tcc  tac  ctc  ttt  acc  ttg  aat  gat  cag    1825
Ile  Glu  Asp  Arg  Ile  Gly  Ser  Ser  Tyr  Leu  Phe  Thr  Leu  Asn  Asp  Gln
          590                      595                      600 ctc  gaa  atc  gat  gct  cgc  cgt  aaa  gga  aac  gag  ttc  aaa  ttt  ctc  aat    1873
Leu  Glu  Ile  Asp  Ala  Arg  Arg  Lys  Gly  Asn  Glu  Phe  Lys  Phe  Leu  Asn
605                      610                      615                      620 cac  tca  gca  aga  cct  aac  tgc  tac  gcc  aag  ttg  atg  att  gtg  aga  gga    1921
His  Ser  Ala  Arg  Pro  Asn  Cys  Tyr  Ala  Lys  Leu  Met  Ile  Val  Arg  Gly
                    625                      630                      635 gat  cag  agg  att  ggt  cta  ttt  gcg  gag  aga  gca  atc  gaa  gaa  ggt  gag    1969
Asp  Gln  Arg  Ile  Gly  Leu  Phe  Ala  Glu  Arg  Ala  Ile  Glu  Glu  Gly  Glu
               640                      645                      650 gag  ctt  ttc  ttc  gac  tac  tgc  tat  gga  cca  gaa  cat  gcg  gat  tgg  tcg    2017
Glu  Leu  Phe  Phe  Asp  Tyr  Cys  Tyr  Gly  Pro  Glu  His  Ala  Asp  Trp  Ser
          655                      660                      665 cgt  ggt  cga  gaa  cct  aga  aag  act  ggt  gct  tct  aaa  agg  tct  aag  gaa    2065
Arg  Gly  Arg  Glu  Pro  Arg  Lys  Thr  Gly  Ala  Ser  Lys  Arg  Ser  Lys  Glu
670                      675                      680 gcc  cgt  cca  gct  cgt  tag  tttttgatct  gaggagaagc  agcaattcaa               2113
Ala  Arg  Pro  Ala  Arg
685                 690 gcagtccttt ttttatgtta tggtatatca attaataatg taatgctatt ttgtgttact              2173
aaaccaaaac ttaagtttct gttttatttg ttttagggtg ttttgtttgt atcatatgtg              2233
tcttaacttt caaagttttc ttttgtatt tcaatttaaa acaatgtttt atgttgttaa               2293
aaaaaaaaaa aaaaaactcg ag                                                       2315
```

<210> SEQ ID NO 2
<211> LENGTH: 689
<212> TYPE: PRT
<213> ORGANISM: Artificial Sequence
<220> FEATURE:
<223> OTHER INFORMATION: Description of Artificial Sequence: MEAwt

<400> SEQUENCE: 2

```
Met Glu Lys Glu Asn His Glu Asp Asp Gly Glu Gly Leu Pro Pro Glu
 1               5                  10                  15

Leu Asn Gln Ile Lys Glu Gln Ile Glu Lys Glu Arg Phe Leu His Ile
            20                  25                  30

Lys Arg Lys Phe Glu Leu Arg Tyr Ile Pro Ser Val Ala Thr His Ala
        35                  40                  45

Ser His His Gln Ser Phe Asp Leu Asn Gln Pro Ala Ala Glu Asp Asp
    50                  55                  60

Asn Gly Gly Asp Asn Lys Ser Leu Leu Ser Arg Met Gln Asn Pro Leu
65                  70                  75                  80

Arg His Phe Ser Ala Ser Ser Asp Tyr Asn Ser Tyr Glu Asp Gln Gly
                85                  90                  95

Tyr Val Leu Asp Glu Asp Gln Asp Tyr Ala Leu Glu Glu Asp Val Pro
            100                 105                 110

Leu Phe Leu Asp Glu Asp Val Pro Leu Leu Pro Ser Val Lys Leu Pro
        115                 120                 125

Ile Val Glu Lys Leu Pro Arg Ser Ile Thr Trp Val Phe Thr Lys Ser
    130                 135                 140
```

-continued

```
Ser Gln Leu Met Ala Glu Ser Asp Ser Val Ile Gly Lys Arg Gln Ile
145                 150                 155                 160

Tyr Tyr Leu Asn Gly Glu Ala Leu Glu Leu Ser Ser Glu Glu Asp Glu
                165                 170                 175

Glu Asp Glu Glu Glu Asp Glu Glu Ile Lys Lys Glu Lys Cys Glu
                180                 185                 190

Phe Ser Glu Asp Val Asp Arg Phe Ile Trp Thr Val Gly Gln Asp Tyr
                195                 200                 205

Gly Leu Asp Asp Leu Val Val Arg Arg Ala Leu Ala Lys Tyr Leu Glu
                210                 215                 220

Val Asp Val Ser Asp Ile Leu Glu Arg Tyr Asn Glu Leu Lys Leu Lys
225                 230                 235                 240

Asn Asp Gly Thr Ala Gly Glu Ala Ser Asp Leu Thr Ser Lys Thr Ile
                245                 250                 255

Thr Thr Ala Phe Gln Asp Phe Ala Asp Arg Arg His Cys Arg Arg Cys
                260                 265                 270

Met Ile Phe Asp Cys His Met His Glu Lys Tyr Glu Pro Glu Ser Arg
                275                 280                 285

Ser Ser Glu Asp Lys Ser Ser Leu Phe Glu Asp Glu Asp Arg Gln Pro
                290                 295                 300

Cys Ser Glu His Cys Tyr Leu Lys Val Arg Ser Val Thr Glu Ala Asp
305                 310                 315                 320

His Val Met Asp Asn Asp Asn Ser Ile Ser Asn Lys Ile Val Val Ser
                325                 330                 335

Asp Pro Asn Asn Thr Met Trp Thr Pro Val Glu Lys Asp Leu Tyr Leu
                340                 345                 350

Lys Gly Ile Glu Ile Phe Gly Arg Asn Ser Cys Asp Val Ala Leu Asn
                355                 360                 365

Ile Leu Arg Gly Leu Lys Thr Cys Leu Glu Ile Tyr Asn Tyr Met Arg
                370                 375                 380

Glu Gln Asp Gln Cys Thr Met Ser Leu Asp Leu Asn Lys Thr Thr Gln
385                 390                 395                 400

Arg His Asn Gln Val Thr Lys Lys Val Ser Arg Lys Ser Ser Arg Ser
                405                 410                 415

Val Arg Lys Lys Ser Arg Leu Arg Lys Tyr Ala Arg Tyr Pro Pro Ala
                420                 425                 430

Leu Lys Lys Thr Thr Ser Gly Glu Ala Lys Phe Tyr Lys His Tyr Thr
                435                 440                 445

Pro Cys Thr Cys Lys Ser Lys Cys Gly Gln Gln Cys Pro Cys Leu Thr
                450                 455                 460

His Glu Asn Cys Cys Glu Lys Tyr Cys Gly Cys Ser Lys Asp Cys Asn
465                 470                 475                 480

Asn Arg Phe Gly Gly Cys Asn Cys Ala Ile Gly Gln Cys Thr Asn Arg
                485                 490                 495

Gln Cys Pro Cys Phe Ala Ala Asn Arg Glu Cys Asp Pro Asp Leu Cys
                500                 505                 510

Arg Ser Cys Pro Leu Ser Cys Gly Asp Gly Thr Leu Gly Glu Thr Pro
                515                 520                 525

Val Gln Ile Gln Cys Lys Asn Met Gln Phe Leu Leu Gln Thr Asn Lys
                530                 535                 540

Lys Ile Leu Ile Gly Lys Ser Asp Val His Gly Trp Gly Ala Phe Thr
545                 550                 555                 560

Trp Asp Ser Leu Lys Lys Asn Glu Tyr Leu Gly Glu Tyr Thr Gly Glu
```

-continued

```
                           565                 570                 575
Leu Ile Thr His Asp Glu Ala Asn Glu Arg Gly Arg Ile Glu Asp Arg
                580                 585                 590
Ile Gly Ser Ser Tyr Leu Phe Thr Leu Asn Asp Gln Leu Glu Ile Asp
            595                 600                 605
Ala Arg Arg Lys Gly Asn Glu Phe Lys Phe Leu Asn His Ser Ala Arg
        610                 615                 620
Pro Asn Cys Tyr Ala Lys Leu Met Ile Val Arg Gly Asp Gln Arg Ile
625                 630                 635                 640
Gly Leu Phe Ala Glu Arg Ala Ile Glu Glu Gly Glu Leu Phe Phe
                645                 650                 655
Asp Tyr Cys Tyr Gly Pro Glu His Ala Asp Trp Ser Arg Gly Arg Glu
                660                 665                 670
Pro Arg Lys Thr Gly Ala Ser Lys Arg Ser Lys Glu Ala Arg Pro Ala
            675                 680                 685
Arg
```

<210> SEQ ID NO 3
<211> LENGTH: 2327
<212> TYPE: DNA
<213> ORGANISM: Artificial Sequence
<220> FEATURE:
<223> OTHER INFORMATION: Description of Artificial Sequence: MEA1
<221> NAME/KEY: variation
<222> LOCATION: (1760)..(1761)

<400> SEQUENCE: 3

```
aggcgagtgg ttaatggaga aggaaaacca tgaggacgat ggtgagggtt tgccacccga      60
actaaatcag ataaaagagc aaatcgaaaa ggagagattt ctgcatatca agagaaaatt     120
cgagctgaga tacattccaa gtgtggctac tcatgcttca caccatcaat cgtttgactt     180
aaaccagccc gctgcagagg atgataatgg aggagacaac aaatcacttt tgtcgagaat     240
gcaaaaccca cttcgtcatt tcagtgcctc atctgattat aattcttacg aagatcaagg     300
ttatgttctt gatgaggatc aagattatgc tcttgaagaa gatgtaccat tatttcttga     360
tgaagatgta ccattattac caagtgtcaa gcttccaatt gttgagaagc taccacgatc     420
cattacatgg gtcttcacca aaagtagcca gctgatggct gaaagtgatt ctgtgattgg     480
taagagacaa atctattatt tgaatggtga ggcactagaa ttgagcagtg aagaagatga     540
ggaagatgaa gaagaagatg aggaagaaat caagaaagaa aaatgcgaat tttctgaaga     600
tgtagaccga tttatatgga cggttgggca ggactatggt ttggatgatc tggtcgtgcg     660
gcgtgctctc gccaagtacc tcgaagtgga tgtttcggac atattggaaa gatacaatga     720
actcaagctt aagaatgatg gaactgctgg tgaggcttct gatttgacat ccaagacaat     780
aactactgct ttccaggatt ttgctgatag acgtcattgc cgtcgttgca tgatattcga     840
ttgtcatatg catgagaagt atgagcccga gtctagatcc agcgaagaca aatctagttt     900
gtttgaggat gaagatagac aaccatgcag tgagcattgt tacctcaagg tgaggagtgt     960
gacagaagct gatcatgtga tggataatga taactctata tcaaacaaga ttgtggtctc    1020
agatccaaac aacactatgt ggacgcctgt agagaaggat cttttacttga aaggaattga    1080
gatatttggg agaaacagtt gtgatgttgc attaaacata cttcgggggc ttaagacgtg    1140
cctagagatt tacaattaca tgcgcgaaca agatcaatgt actatgtcat tagaccttaa    1200
caaaactaca caaagacaca atcaggttac caaaaaagta tctcgaaaaa gtagtaggtc    1260
```

-continued

```
ggtccgcaaa aaatcgagac tccgaaaata tgctcgttat ccgcctgctt taaagaaaac     1320
aactagtgga gaagctaagt tttataagca ctacacacca tgcacttgca agtcaaaatg     1380
tggacagcaa tgcccttgtt taactcacga aaattgctgc gagaaatatt gcgggtgctc     1440
aaaggattgc aacaatcgct ttggaggatg taattgtgca attggccaat gcacaaatcg     1500
acaatgtcct tgttttgctg ctaatcgtga atgcgatcca gatctttgtc ggagttgtcc     1560
tcttagctgt ggagatggca ctcttggtga gacaccagtg caaatccaat gcaagaacat     1620
gcaattcctc cttcaaacca ataaaaagat tctcattgga aagtctgatg ttcatggatg     1680
gggtgcattt acatgggact ctcttaaaaa gaatgagtat ctcggagaat atactggaga     1740
actgatcact cactcatgat ctcatgatga agctaatgag cgtgggagaa tagaagatcg     1800
gattggttct tcctacctct ttaccttgaa tgatcagctc gaaatcgatg ctcgccgtaa     1860
aggaaacgag ttcaaatttc tcaatcactc agcaagacct aactgctacg ccaagttgat     1920
gattgtgaga ggagatcaga ggattggtct atttgcggag agagcaatcg aagaaggtga     1980
ggagcttttc ttcgactact gctatggacc agaacatgcg gattggtcgc gtggtcgaga     2040
acctagaaag actggtgctt ctaaaaggtc taaggaagcc cgtccagctc gttagttttt     2100
gatctgagga gaagcagcaa ttcaagcagt cctttttta tgttatggta tatcaattaa     2160
taatgtaatg ctattttgtg ttactaaacc aaaacttaag tttctgtttt atttgtttta     2220
gggtgttttg tttgtatcat atgtgtctta actttcaaag ttttctttt gtatttcaat     2280 ttaaaaacaa tgtttatgtt gttaaaaaaa aaaaaaaaa actcgag                    2327
```

<210> SEQ ID NO 4
<211> LENGTH: 2322
<212> TYPE: DNA
<213> ORGANISM: Artificial Sequence
<220> FEATURE:
<223> OTHER INFORMATION: Description of Artificial Sequence: MEA2
<221> NAME/KEY: variation
<222> LOCATION: (1756)..(1763)

<400> SEQUENCE: 4

```
aggcgagtgg ttaatggaga aggaaaacca tgaggacgat ggtgagggtt tgccacccga      60
actaaatcag ataaaagagc aaatcgaaaa ggagagattt ctgcatatca agagaaaatt     120
cgagctgaga tacattccaa gtgtggctac tcatgcttca caccatcaat cgtttgactt     180
aaaccagccc gctgcagagg atgataatgg aggagacaac aaatcacttt tgtcgagaat     240
gcaaaaccca cttcgtcatt tcagtgcctc atctgattat aattcttacg aagatcaagg     300
ttatgttctt gatgaggatc aagattatgc tcttgaagaa gatgtaccat atttcttga     360 tgaagatgta ccattattac caagtgtcaa gcttccaatt gttgagaagc taccacgatc     420
cattacatgg gtcttcacca aaagtagcca gctgatggct gaaagtgatt ctgtgattgg     480
taagagacaa atctattatt tgaatggtga ggcactagaa ttgagcagtg aagaagatga     540
ggaagatgaa gaagaagatg aggaagaaat caagaaagaa aaatgcgaat tttctgaaga     600
tgtagaccga tttatatgga cggttgggca ggactatggt ttggatgatc tggtcgtgcg     660
gcgtgctctc gccaagtacc tcgaagtgga tgtttcggac atattggaaa gatcaatga    720 actcaagctt aagaatgatg gaactgctgg tgaggcttct gatttgacat ccaagacaat     780
aactactgct ttccaggatt ttgctgatag acgtcattgc cgtcgttgca tgatattcga     840
ttgtcatatg catgagaagt atgagcccga gtctagatcc agcgaagaca aatctagttt     900
gtttgaggat gaagatagac aaccatgcag tgagcattgt tacctcaagg tgaggagtgt     960
```

```
gacagaagct gatcatgtga tggataatga taactctata tcaaacaaga ttgtggtctc   1020
agatccaaac aacactatgt ggacgcctgt agagaaggat ctttacttga aaggaattga   1080
gatatttggg agaaacagtt gtgatgttgc attaaacata cttcgggggc ttaagacgtg   1140
cctagagatt tacaattaca tgcgcgaaca agatcaatgt actatgtcat tagaccttaa   1200
caaaactaca caaagacaca atcaggttac caaaaaagta tctcgaaaaa gtagtaggtc   1260
ggtccgcaaa aaatcgagac tccgaaaata tgctcgttat ccgcctgctt taagaaaac    1320 aactagtgga gaagctaagt tttataagca ctacacacca tgcacttgca agtcaaaatg   1380
tggacagcaa tgcccttgtt taactcacga aaattgctgc gagaaatatt gcgggtgctc   1440
aaaggattgc aacaatcgct ttggaggatg taattgtgca attggccaat gcacaaatcg   1500
acaatgtcct tgttttgctg ctaatcgtga atgcgatcca gatctttgtc ggagttgtcc   1560
tcttagctgt ggagatggca ctcttggtga gacaccagtg caaatccaat gcaagaacat   1620
gcaattcctc cttcaaacca ataaaaagat tctcattgga aagtctgatg ttcatggatg   1680
gggtgcattt acatgggact ctcttaaaaa gaatgagtat ctcggagaat atactggaga   1740
actgatcact catgaatcat gatgaagcta atgagcgtgg gagaatagaa gatcggattg   1800
gttcttccta cctctttacc ttgaatgatc agctcgaaat cgatgctcgc cgtaaaggaa   1860
acgagttcaa atttctcaat cactcagcaa gacctaactg ctacgccaag ttgatgattg   1920
tgagaggaga tcagaggatt ggtctatttg cggagagagc aatcgaagaa ggtgaggagc   1980
ttttcttcga ctactgctat ggaccagaac atgcggattg gtcgcgtggt cgagaaccta   2040
gaaagactgg tgcttctaaa aggtctaagg aagcccgtcc agctcgttag ttttttgatct  2100 gaggagaagc agcaattcaa gcagtccttt ttttatgtta tggtatatca attaataatg   2160
taatgctatt ttgtgttact aaaccaaaac ttaagtttct gttttatttg ttttagggtg   2220
ttttgtttgt atcatatgtg tcttaacttt caaagttttc tttttgtatt tcaatttaaa   2280
aacaatgttt atgttgttaa aaaaaaaaaa aaaaaactcg ag                      2322
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 5
ccgtttaccg ttttgtatat cccg                                           24

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: synthetic
      primer

<400> SEQUENCE: 6
cgttccgttt cgttttttta cc                                             22

<210> SEQ ID NO 7
<211> LENGTH: 21
<212> TYPE: DNA
<213> ORGANISM: Artificial Sequence
<220> FEATURE:

```
<223> OTHER INFORMATION: Description of Artificial Sequence: synthetic
      primer

<400> SEQUENCE: 7
ggtcggtacg gcaattctcc c                                              21

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 8
cgattaccgt atttatcccg ttcg                                           24

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: synthetic
      primer

<400> SEQUENCE: 9
ccggtatatc ccgttttcg                                                 19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 10
gttaccgacc gttttcatcc                                                20

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: synthetic
      primer

<400> SEQUENCE: 11
ccagcagttc catcattc                                                  18

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: synthetic
      primer

<400> SEQUENCE: 12
gtccgaaaca tccacttcg                                                 19

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: synthetic
``` primer

<400> SEQUENCE: 13
cgaccagatc atccaaacca tag                                       23

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: synthetic
      primer

<400> SEQUENCE: 14
cgtagcagtt aggtcttgc                                            19

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: synthetic
      primer

<400> SEQUENCE: 15
cgtcgacccg tcaggactct c                                         21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 16
gcaggactat ggtttggatg                                           20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: synthetic
      primer

<400> SEQUENCE: 17
caccttgagg taacaatgct c                                         21

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: synthetic
      primer

<400> SEQUENCE: 18
aactttcaac actcctgcca tg                                        22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: synthetic
      primer -continued

```
<400> SEQUENCE: 19
ctgcaaggtc caaacgcaga                                              20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: synthetic
      primer

<400> SEQUENCE: 20
gagccagttt gtgtttgc                                                18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: synthetic
      primer

<400> SEQUENCE: 21
taaggaggga agaaaggg                                                18
```

SEED SPECIFIC POLYCOMB GROUP GENE AND METHODS OF USE FOR SAME

FIELD OF THE INVENTION

This invention relates to the isolation and characterization of a Polycomb gene from Arabidopsis with control of seed specific cell proliferation (wild type expressed as MEA). The novel gene and gene product may be used to manipulate embryo and endosperm cell proliferation for the generation of parthenocarpy, seed specific characteristics, control of undesirable seed production, or apomixis in Arabidopsis and other plant types. Two mutations of this gene (mutant forms expressed as mea) have also been identified which cause maternal effect embryo lethality.

BACKGROUND OF THE INVENTION

The plant life cycle alternates between a diploid and a haploid generation, the sporophyte and the gametophyte. Unlike in animals where meiotic products differentiate directly into gametes, the plant spores undergo several divisions to form a multicellular organism. Differentiation of the gametes occurs later in gametophyte development.

Reproduction in plants is ordinarily classified as sexual or asexual. The term apomixis is generally accepted as the replacement of sexual reproduction by various forms of asexual reproduction (Rieger et al., IN Glossary of Genetics and Cytogenetics, Springer-Verlag, New York, N.Y., 1976). In general the initiation of cell proliferation in the embryo and endosperm are uncoupled from fertilization. Apomixis is a genetically controlled method of reproduction in plants where the embryo is formed without union of an egg and a sperm. There are three basic types of apomictic reproduction: 1) apospory-embryo develops from a chromosomally unreduced egg in an embryo sac derived from a somatic cell in the nucellus, 2) diplospory-embryo develops from an unreduced egg in an embryo sac derived from the megaspore mother cell, and 3) adventitious embryony-embryo develops directly from a somatic cell. In most forms of apomixis, pseudogamy or fertilization of the polar nuclei to produce endosperm is necessary for seed viability. These types of apomixis have economic potential because they can cause any genotype, regardless of how heterozygous, to breed true. It is a reproductive process that bypasses female meiosis and syngamy to produce embryos genetically identical to the maternal parent. With apomictic reproduction, progeny of specially adaptive or hybrid genotypes would maintain their genetic fidelity throughout repeated life cycles. In addition to fixing hybrid vigor, apomixis can make possible commercial hybrid production in crops where efficient male sterility or fertility restoration systems for producing hybrids are not known or developed. Apomixis can make hybrid development more efficient. It also simplifies hybrid production and increases genetic diversity in plant species with good male sterility.

In sexual reproduction, usually a megaspore mother cell arising from the hypodermal layer of the ovule enlarges and goes through meiosis and two cell divisions to form a linear tetrad of megaspores each with a haploid chromosome number. The three micropylar spores degenerate while the functional chalazal spore enlarges to form an embryo sac with an egg, two polar nuclei, two synergids, and three antipodals.

Introducing the apomictic trait into normally sexual crops has been attempted. Asker (Heredias, Vol. 91, 231–241, 1979) reports that attempts have been unsuccessful with wheat, sugar beets, and maize. PCT publication WO 89/00810 (Maxon et al, 1989) discloses inducing an apomictic form of reproduction in cultivated plants using extracts from nondomesticated sterile alfalfa plants. When induction of male sterility was evaluated in sorghum, sunflower, pearl millet, and tomato it was reported that there was reduced seed set in sorghum, pearl millet, and sunflower and reduced fruit set in tomato.

It would be ideal to find genes controlling obligate or a high level of apomixis in the cultivated species and be able to readily hybridize cross-compatible sexual x apomictic genotypes to produce true-breeding $F_1$ hybrids. In reality, most desirable genes controlling apomixis are found in the wild species which are distantly related to the cultivated species. Although interspecific crosses may be possible between the cultivated and wild species, chromosome pairing between genomes is usually low or nonexistent.

Although apomixis is effectively used in Citrus to produce uniform and disease- and virus-free rootstock (Parlevliet JE et al, in *Citrus. Proc. Am. Soc. Hort. Sci.*, Vol. 74, 252–260, 1959) and in buffelgrass (Bashaw, *Crop Science*, Vol. 20, 112, 1980) and Poa (Pepin et al, *Crop Science*, Vol. 11, 445–448, 1971) to produce improved cultivars, it has not been successfully transferred to a cultivated crop plant. The transfer of apomixis to important crops would make possible development of true-breeding hybrids and commercial production of hybrids without a need for cytoplasmic-nuclear male sterility and high cost, labor-intensive production processes. An obligately apomictic $F_1$ hybrid would breed true through the seed indefinitely and could be considered a vegetative or clonal method of reproduction through the seed. The development of apomictically reproducing cultivated crops would also provide a major contribution toward the food security in developing nations (Wilson et al, IN Proceedings of the International Workshop on Apomixis in Rice, Changsha, People's Republic of China, Jan. 13–Jan. 15, 1992. Hunan Hybrid Rice Research Center, Changsha, People's Republic of China).

The generation of apomixis is only one of the many potential benefits of controlling cell proliferation in the embryo or endosperm portions of the seed. Induction of parthenocarpy for seedless fruits and vegetables or the production of value added custom seeds which involve enhancement of certain tissue areas at the expense of others is another. As can be seen from the foregoing, there is a need in the art for tissue specific control of cell proliferation.

It is thus an object of the present invention to provide a novel gene and protein which regulate cell proliferation in a tissue specific manner.

It is yet another object of the invention to provide a DNA sequence which encodes a gene from the Polycomb family from Arabidopsis which is involved with initiation and control of embryo and endosperm cell proliferation.

A further object is to provide a mechanism to manipulate embryo and endosperm cell proliferation to achieve apomixis or fertilization independent cell proliferation.

A further object of the present invention is to provide constructs for expression of or inhibition of this gene product.

A further object of the invention is to provide a method for controlling undesirable seed production through the use of a suicide gene.

Finally, it is an object of the present invention to provide genetic material which can used to screen other genomes to identify other genes with similar effects from other plant sources or even from animal sources.

SUMMARY OF THE INVENTION

According to the invention a novel gene from the Polycomb family has been isolated and characterized from Arabidopsis. This gene (MEDEA or abbreviated MEA both of which reference the wild-type form of the gene) encodes a SET domain protein similar to Enhancer of zeste of Drosophila. Polycomb group proteins also occur in animals and are highly conserved and ensure the stable inheritance of expression patterns through cell division as well as controlling cell proliferation.

The gene encodes a protein product which is intimately involved in the regulation of cell proliferation, particularly in the embryo and endosperm. Two mutants with disruptions in the SET domain region of this gene demonstrated aberrant growth regulation during embryogenesis. Embryos derived from mutant eggs grew excessively and died during seed desiccation. This lethality was independent of parental contribution and gene dosage.

Thus the novel gene and protein product of the invention provide a valuable tool for the manipulation of seed development and embryogenesis to induce parthenocarpy, apomixis, seed sterility or even to engineer the specific tissue and thus content of valuable components of seeds. Genetic engineering methods known in the art can be used to inhibit expression of the gene or to further induce expression thus controlling the developmental effects regulated thereby, in not only Arabidopsis but other plants and animals. Further, due to the highly conserved nature of this family of genes, particularly in the SET domain, and in the CXC domain it is expected that other such genes may be identified using the DNA and amino acid sequences herein to characterize other closely related genes from other species. As used herein, the term SET domain and CXC shall include the domains as described in the references incorporated herein or any other sequence substantially equivalent thereto.

DETAILED DESCRIPTION OF THE FIGURES

The file of this patent contains at least one drawing executed in color. Copies of this patent with color drawing(s) will be provided by the Patent and Trademark Office upon request and payment of the necessary fee.

FIG. 1 is the cDNA sequence encoding the novel Polycomb gene of the invention, wild-type MEA, SEQ ID NO:1.

FIG. 2(A) shows self-pollinated silique. Half of the seeds have collapsed and turned brown.

FIG. 2(B) shows slightly younger silique derived from a cross between mea (female) and a wild type plant (male) of the Columbia (Col) ecotype. Seeds derived from mea gametes are white and start collapsing.

FIG. 2(C) shows silique derived from a cross between Col (female) and mea (male) (bar=215 μm).

Figure 2:
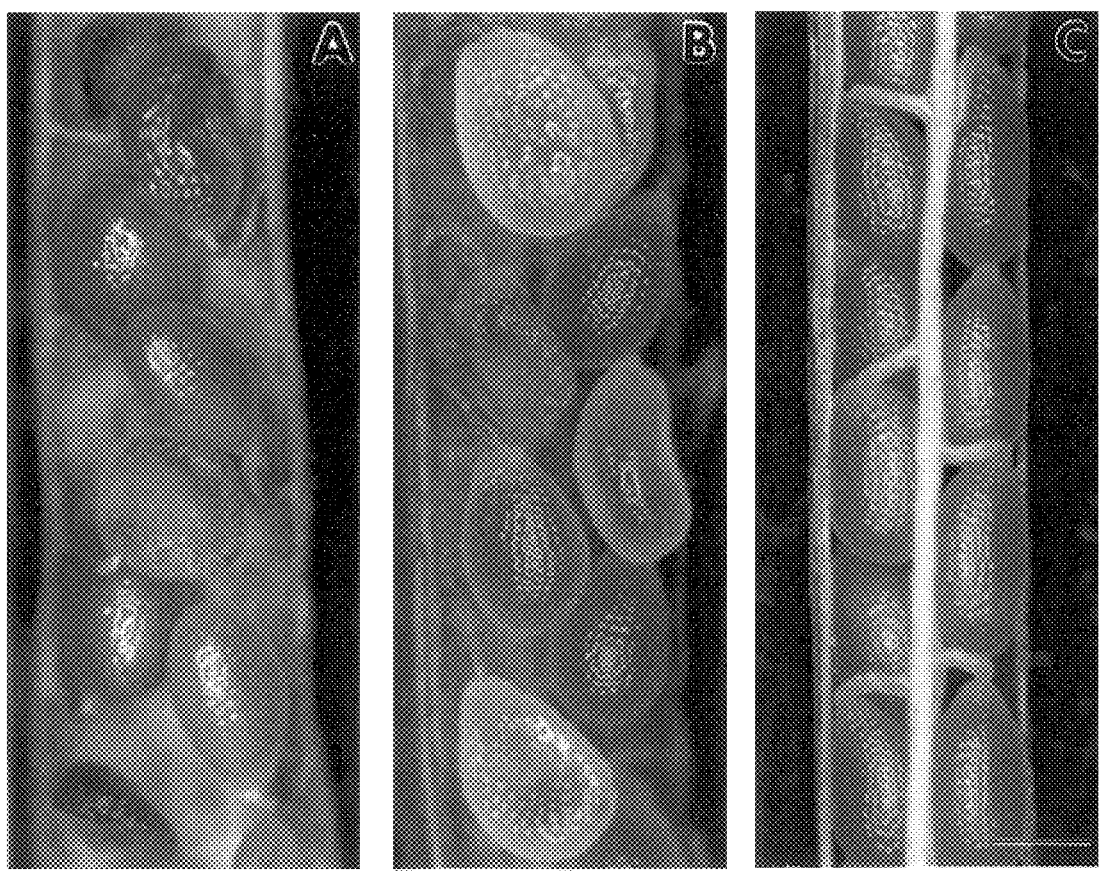
FIG. 2A–2C are photographs depicting the seed phenotype of mea in immature siliques.

FIG. 3A–3H are photographs depicting embryo development in mea plants. Comparison of wild type (A, C, E and G) and mea (B, D, F, and H) embryos at equivalent developmental stages. Histological analysis was conducted in heterozygous mea plants at different developmental stages using semi-thin sections (A and B) and cleared seeds (C to H).

FIG. 3(A): Late globular wild type embryo.

FIG. 3(B): Late globular mea embryo.

FIG. 3(C): Mid-globular wild type embryo.

FIG. 3(D): Mid-globular mea embryo.

FIG. 3(E): Early heart stage wild type embryo.

FIG. 3(F): Early heart stage mea embryo.

FIG. 3(G): Late heart stage wild type embryo.

FIG. 3(H): Late heart stage mea embryo.

FIGS. 3(A) and 3(B) are at the same magnification (bar=12 μm); FIGS. 3(C) to 3(H) are all at the same magnification (bar=40 μm).

FIG. 4(A) shows deduced amino acid sequence of MEA. A highly acidic region is underlined. A similar acidic stretch is also found in the trx protein. The five cysteines which are highly conserved in all E(z) homologs are in boldface, and the 18 cysteine residues of the CXC domain are in boldface and underlined. Basic residues of a putative bipartite nuclear localization signal are indicated by asterisks. The 115 amino acids of the SET domain are boxed.

FIG. 4(B) is a schematic alignment of MEA and E(z) showing the relative position and amino acid identity of the SET and CXC domains, the putative nuclear localization signals (N), the five conserved cysteines ($C_5$), and the highly acidic domain (A).

FIG. 4(D) is an RT-PCR analysis of MEA during flower and seed development. The three panels show amplification of MEA, and actin-11 (ACT11) and the seed storage protein At2S2 as controls for cDNA synthesis (J. M. McDowell et al., Genetics 142, 587 (1996); P. Guerche et al., Plant Cell 2, 469 (1990)). RNA was isolated from floral buds (B), unpollinated carpels (U), pollinated carpels (P), siliques containing embryos at the pre-globular (PG), globular (G), heart (H), torpedo to early cotyledonary (T/C), cotyledonary (C), early (EM) and late maturation (LM) stages. (M) indicates the marker lane and (G) genomic DNA as a control.

FIG. 4(C) depicts DNA sequences flanking the mea-1 Ds insertion and derivative alleles. The 8 base pair target site duplication in indicated in boldface. All revertants analyzed showed the wild type sequence. In the stable mea-2 excision allele a 7 base pair footprint remains; an additional base is altered (underlined). The mea-2 footprint introduces two stop codons (lower case).

DETAILED DESCRIPTION OF THE INVENTION

Polycomb group genes regulate the expression of homeotic genes as well as cellular proliferation. In the development of multicellular organisms, the process of determination requires the maintenance of specific patterns of gene expression through many cycles of cell division.

Homeotic genes specify the identity of serially repeated units such as the whorls of flowers or the segments of insects (Coch, E. S., et al., "The war of the whorla genetic interactions controlling flower development", *Nature,* 353:31–37 (1991); Lewis, "A gene complex controlling segmentation in Drosophila, *Nature* 276:565–570 (1978)). In both plants and animals they are transcribed in precise spatial patterns, often throughout development, and the particular combination of genes active in a cell specifies its identity. In several cases, expression late in development is both necessary and sufficient to specify identity (Bowman, J. L., "Genes directing flower development in Arabidopsis", *Plant Cell,* 1, 37–52 (1989; Carpenter, R, et al., "Floral homeotic mutations produced by transposon-mutagenesis in . . . ", *Genes Dev.,* 4:1483–1493 (1990); Struhl, G., "Genes controlling segmentation specification in the Drosophila thorax", *Proc. Natl Acad. Sci. USA,* 79:7360–7384 (1982)). Because homeotic gene expression patterns are specified early in development as a result of complex genetic interactions (reviewed in refs Ingham, P. W., "The molecular genetics of embryonic pattern formation in Drosophila", *Nature,* 335:25–33 (1988); Weigel, "The ABCs of doral homeotic genes", *Cell,* 78:203–209 (1994)), this raises the problem of how these patterns are faithfully maintained and propagated through cell divisions during later development.

In Drosophila embryogenesis, regional fate becomes determined early, at around the cellular blastoderm stage (Simons, A., "When does determination occur in Drosophila embryos", *Dev. Biol.,* 97:212–221 (1983)), and alternative fates are selected and determined by the persistent activity of homeotic genes (Lawrence, P. A., IN Insect Development, ed. Lawrence, P. A. 132–148 (Blackwell, Oxford, 1976)). The maintenance of expression boundaries during later stages of development requires the activity of two antagonistic groups of genes, the Polycomb-group (Pc-G) and the trithorax-group (trx-G) (Simon, J., "Locking in stable states of gene expression: transcriptional control during Drosophila development", *Curr. Opin. Cell Hint.,* 7:376–385 (1995); Kennison, J. A., "Transcriptional activation of Drosophila homeotic genes from distant regulatory elements", *Trends Genec.* 9:75–79 (1993)).

Polycomb group (Pc-G) genes and trithorax group in Drosophila encode transacting factors that are responsible for preventing the transcription of homeotic selector (HOM-C) genes outside of their appropriate expression domains through positive and negative regulation (Duncan and Lewis, 1982; Struhl and Akam, 1985; Paro, 1990). There are several criteria according to which genes are classified as members of the Polycomb group. Loss-of-function mutations in Pc-G genes produce phenotypes similar to those caused by loss of Polycomb function. In embryos, this results in the disruption of the anterior/posterior expression boundaries of HOM-C genes of the ANTP-C and BX-C leading to ectopic expression of abd-A and Abd-B (Simon et al., 1992) and transformation of the thoracic and abdominal segments to the identity of the eighth abdominal segment.

Enhancer of zeste (E(z)) has been classified as a Pc-G gene (Jones and Gelbart, 1990; Phillips and Shearn, (1990). A loss-of-function allele of the E(z) gene was recovered in a screen for late larval/pupal recessive lethal mutations that cause imaginal disc abnormalities (Shearn et al., 1971). It also however exhibits several properties of the trithorax group as well (LaJeunesse and Shearn 1996).

In plants, the role of homeotic genes is best understood with respect to flower development. Flowers typically contain four concentric whorls of organs with identity sepal (whorl 1), petal (whorl 2), stamen (whorl 3) and carpel (whorl 4). Based on the genetic and morphological analysis of floral homeotic mutants, a model has been proposed to account for the specification of organ identity in the different whorls based on combinatorial action of homeotic genes (Coch, E. S., et al., "The war of the whorla genetic interactions controlling flower development", *Nature,* 353:31–37 (1991)). In Arabidopsis, the homeotic AGAMOUS (AG) gene is required to specify stamen and carpal identity in whorls 3 and 4 respectively. Molecular isolation of the AG gene indicates that it encodes a protein belonging to the MADS box family of transcription factors, and that its RNA is confined to its domain of function in whorls 3 and 4 (Yanofsky, M. F., et al., "The protein encoded by the Arabidopsis homeotic gene AGAMOUS resembles transcription factors", *Nature,* 346:35–39 (1990); Drews, G. N., "Negative regulation of the Arabidopsis homeotic gene AGAMOUS by the APETALA2 product", *Cell,* 63:991–1002 (1991)).

Applicants have discovered a Polycomb group gene isolated from Arabidopsis that is involved in cell proliferation associated with seed development. If the MEA gene product is missing, embryos overproliferate and the endosperm underproliferates. Thus, the MEA gene and protein product can regulate proliferation both negatively and positively depending on the tissue. The wild type protein restricts embryo growth but promotes endosperm proliferation. A role in the control of cell proliferation either positively or negatively has also been shown for some of the animal homologs and this aspect of SET domain protein function appears to be conserved. (Simon, J., "Locking in stable states of gene expression: transcriptional control during Drosophila development", *Curr Opin. Cell Biol.* Vol. 7, 376–385 (1995)).

Thus in one embodiment of the invention, the gene or its protein product can be used in regulation of cell proliferation, both if overexpressed or if the activity is suppressed as for instance by antisense expression, homologous recombination or co-suppression mechanisms. The effect is different in different tissues. More specifically, the gene or its gene product can be used to control seed expression to tailor seeds to specific requirements. For example inhibiting MEA expression results in extremely large seeds by stimulating embryo expression at the expense of endosperm. This will result in seeds with higher content of valuable components such as proteins or oils and in the case of higher protein content seeds will increase feed efficiency for seeds used as animal feed. Thus proteins expressed in the embryo can have increased production for harvesting.

On the other hand several valuable proteins are found in the endosperm of plants. The endosperm in Arabidopsis is transient and almost completely absent in a mature seed. Hence, as in most species with a transient endosperm, it is the embryo that accumulates high contents of protein and lipid bodies. (Bergfield et al., 1978, "Formation of oleosomes (storage lipids) during embryogenesis and their breakdown during seedling development in cotyledons of Sinapis alba", *L. Planta,* 143, 297–307; Tykarska, 1987a, "Rape embryogenesis. V. Accumulation of lipid bodies", *Acta Soc. Bot. Poloniae,* 56, 573–584; Higgins, "Synthesis and regulation of proteins in seeds", *Ann Rev. Plant Phys.,* 35, 187–221 (1984); Patton D. A. and Meinke D. W. 1990, "Ultrastructure of arrested embryos from lethal mutants of Arabidopsis thaliana", *Am. J. Bot.,* 77, 653, 661). Lipid bodies in the embryo of Arabidopsis are rich in fatty acids and other oil components extensively used in the agroindustry. Arabidopsis is closely related to *Brassica napus,* a species in which the seeds are used to obtain canola oil. In *B. napus* each seed contains approximately 40% oil with low levels of saturated fat; the remainder of the seed is processed into canola meal which is used as a high protein livestock feed. The embryo of Arabidopsis also contains numerous protein bodies rich in the 2S family of albumins and other nutritious seed storage proteins. (Hofstein, A. V., 1974, "The ultrastructure of seed Brassica species-new sources of seed proteins", *Bot. Tidskr.,* 68, 153–163; Guerche P. et al., 1991, "Differential expression of the Arabidopsis 2S albumin genes and the effect of increasing gene family size", *Plant Cell,* 2, 469–478; 1984). In contrast, all economically important cereals have a persistent endosperm that is present in the mature seed. The endosperm of cereals contains abundant proteins such as prolamines (gliadins, glutenins, or zeins), globulins, and albumins rich in essential amino acids (including methionine, valine, leucine, isoleucine, phenylalanine, triptophane, threonine, and lysine) necessary for human as well as livestock nutrition( Kim et al., 1993, "Expression of storage protein multigene families in developing rice endosperm", *Plant Cell Physiol.,* 34 (4) 595–603;

Misra et al., 1972, "Endosperm protein synthesis in maize mutants with increased lysine content", *Science,* 176, 1425–1426; Lopes and Larkins, 1993, "Endosperm origin, development, and function", *Plant Cell,* 5, 1383–1399). As an example of the importance of essential amino acid content in maize endosperm, differences in the amount of methionine supplied to two-day old chicks can account for up to 50% differences in weight gained over 15 days feeding trials (Messing J, and Fisher H. 1991, "Maternal effect on high methionine levels in hybrid corn", *J Biotech.* 21, 229–238). As described herein MEA positively affects the growth of endosperm at the expense of the embryo. Thus by providing additional copies of the gene in transgenic plants or by direct administration of the protein endosperm growth and products produced therein may be increased. The gene activating or inactivating elements of the invention could also be combined with inducible, or tissue or even constitutive promoters to achieve the desired effect on cell proliferation.

Since MEA is a Polycomb group member it regulates cell proliferation by controlling gene expression of target genes. These genes regulate other genes by controlling higher order chromatin structure and thereby regulating which transcription factors have access to the target genes. There are probably many other target genes MEA regulates that are involved in cell cycle regulation but it acts as a master switch which makes it useful to regulate a coordinated battery of target genes.

Based on the mutant phenotype and the sequence MEA can be used to control proliferation either positively or negatively which would allow a manipulation of seed development for instance to increase seed size, to change the relative contribution of embryo and endosperm to the seed, in some seeds the embryo is valuable in others, it is the endosperm that comprises valuable products.

The MEA gene and gene product could also be used to manipulate cell division in the absence of fertilization. If embryo and/or endosperm development can be initiated that would allow the production of haploid parthenogenetic offspring, a very valuable technique for breeding in crops. This could also result in the production of seedless fruits and vegetables or ones with very diminished seed.

If parthenogenesis is combined with non-reduction of the megaspore mother cell it would result in apomictic reproduction and clonal offspring.

This gene is highly likely to be conserved in many other species. It is a member of a large gene family in Arabidopsis. There are a about 8 other SET domain proteins in the art. MEA is the only one with a known function in seed development, and is at the very least likely to be present in other angiosperm genomes. This is particularly true since its structure and function is conserved even in animals.

The invention herein in its broadest sense contemplates the discovery of the existence of a Polycomb gene in plants that is associated among other things with seed development and/or embryogenesis. The discovery of the existence of this type of gene creates numerous opportunities for manipulation of seed development in plants in general. Due to the highly conserved nature of the gene product, it is expected that this gene or ones substantially equivalent thereto may be identified from other plants with similar seed specific functions. These homologs are intended to be within the scope of this invention. Similarly, the protein product disclosed here also many be used for other plants and many other muteins may be either engineered by those of skill in the art or isolated from other species. Homologous proteins or muteins as described herein and as isolated form other plants are also intended to be within the scope of this invention.

According to the invention a function of the Polycomb MEA gene has been identified as controlling embryogenesis and cell proliferation. Two mutant forms of the gene were created with insertional mutations in the SET region (SEQ ID NO:3 and SEQ ID NO: 4) which caused a nonfunctional protein product which changed the phenotypic effects of the gene. In these two mutations, 50% of the seeds inherit a maternal disrupted copy of the gene and abort irrespective of their paternal parent. Since the mutation is normally transmitted through pollen, the invention can be used as a suicide gene to introduce in Arabidopsis or other undesirable plants present in a population, causing a major decrease in seed set. It is expected that any other loss of function mutation would have similar effects, particularly those which alter the SET regions of the gene. These mutant forms resulted in maternal effect lethality and could be used as a suicide gene to introduce to Arabidopsis, or other undesirable plants present in a population.

This invention further contemplates methods of controlling expression of seed specific Polycomb genes in plants through genetic engineering techniques which are known and commonly used by those of skill in the art. Such methods include but are in no way limited to generation of apomixis, generation of a parthenocarpic phenotype, control of undesirable seeds, generation of seeds engineered to produce higher endosperm or embryo tissue and concomitant higher bioproduct content such as proteins or lipids, as well as other tissue specific regulation based upon expression of the gene at time, spatial and developmental periods.

The term "substantially equivalent" as used herein means that the peptide is a substance having an amino acid with at least 30%–50% homology with at least one form of the protein as disclosed herein. 80% homology is preferred and 90% homology is most preferred especially including conservative substitutions. With respect to a nucleotide sequence the term substantially equivalent means that the sequence will encode a protein or peptide that is substantially equivalent.

Homology is calculated by standard methods which involve aligning two sequences to be compared so that maximum matching occurs, and calculating the percentage of matches. Substantially equivalent substances to these include those wherein one or more of the residues of the native sequence is deleted, substituted for, or inserted by a different amino acid or acids.

Preferred substitutions are those which are conservative, i.e., wherein a residue is replaced by another of the same general type. As is well understood, naturally occurring amino acids can be sub classified as acidic, basic, neutral and polar, or neutral and nonpolar. Furthermore, three of the encoded amino acids are aromatic. It is generally preferred that peptides differing from the native MEA sequence contain substitutions which are from the same group as that of the amino acid replaced. Thus, in general, the basic amino acids Lys and Arg are interchangeable; the acidic amino acids aspartic and glutamic are interchangeable; the neutral polar amino acids Ser, Thr, Cys, Gln, and Asn are interchangeable; the nonpolar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Tyr are interchangeable. While proline is a nonpolar neutral amino acid, it represents difficulties because of its effects on conformation, and substitutions by or for proline are not preferred, except when the same or similar conformational results can be obtained. Polar amino acids which represent conservative changes include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids.

In general, whatever substitutions are made are such that the functional properties of the intact proteinaceous molecule is retained and ancillary properties, such as non-toxicity are not substantially disturbed.

A "structural gene" is a DNA sequence that is transcribed into messenger RNA (mRNA) which is then translated into a sequence of amino acids characteristic of a specific polypeptide.

An "antisense oligonucleotide" is a molecule of at least 6 contiguous nucleotides, preferably complementary to DNA (antigene) or RNA (antisense), which interferes with the process of transcription or translation of endogenous proteins so that gene products are inhibited.

A "promoter" is a DNA sequence that directs the transcription of a structural gene. Typically, a promoter is located in the 5' region of a gene, proximal to the transcriptional start site of a structural gene.

The term "expression" refers to biosynthesis of a gene product. Structural gene expression involves transcription of the structural gene into mRNA and then translation of the mRNA into one or more polypeptides.

The term "Co-suppression" is a method of inhibiting gene expression in plants wherein a construct is introduced to a plant. The construct has one or more copies of sequence which is identical to or which shares nucleotide homology with a resident gene.

"Homologous recombination" is another method of inhibiting gene function by introducing a disruption construct to a plant cell under conditions which facilitate recombination of endogenous genetic material with the construct.

A "cloning vector" is a DNA molecule such as a plasmid, cosmid, or bacterial phage that has the capability of replicating autonomously in a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance or ampicillin resistance.

An "expression vector" is a DNA molecule comprising a gene that is expressed in a host cell. Typically, gene expression is placed under the control of certain regulatory elements including promoters, tissue specific regulatory elements, and enhancers. Such a gene is said to be "operably linked to" the regulatory elements.

A "recombinant host" may be any prokaryotic or eukaryotic cell that contains either a cloning vector or an expression vector. This term also includes those prokaryotic or eukaryotic cells that have been genetically engineered to contain the clone genes in the chromosome or genome of the host cell.

A "transgenic plant" is a plant having one or more plant cells that contain an expression vector. Plant tissue includes differentiated and undifferentiated tissues or plants, including but not limited to roots, stems, shoots, leaves, pollen, seeds, tumor tissue, and various forms of cells and culture such as single cells, protoplasm, embryos, and callus tissue. The plant tissue may be in plant or in organ, tissue, or cell culture.

The invention in one aspect comprises expression constructs comprising a DNA sequence which encodes upon expression a seed specific Polycomb group gene product operably linked to a promoter to direct expression of the protein. These constructs are then introduced into plant cells using standard molecular biology techniques. The invention can be also be used for hybrid plant or seed production, once transgenic inbred parental lines have been established.

In another aspect the invention involves the inhibition of a Polycomb group gene product in plants through introduction of a construct designed to inhibit the same gene product. The design and introduction of such constructs based upon known DNA sequences is known in the art and includes such technologies as antisense RNA or DNA, co-suppression or any other such mechanism. Several of these mechanisms are described and disclosed in U.S. Pat. No. 5,686,649 to Chua et. al, which is hereby expressly incorporated herein by reference.

The methods of the invention described herein may be applicable to any species of plant.

Production of a genetically modified plant tissue either expressing or inhibiting expression of a structural gene combines the teachings of the present disclosure with a variety of techniques and expedients known in the art. In most instances, alternate expedients exist for each stage of the overall process. The choice of expedients depends on the variables such as the plasmid vector system chosen for the cloning and introduction of the recombinant DNA molecule, the plant species to be modified, the particular structural gene, promoter elements and upstream elements used. Persons skilled in the art are able to select and use appropriate alternatives to achieve functionality. Culture conditions for expressing desired structural genes and cultured cells are known in the art. Also as known in the art, a number of both monocotyledonous and dicotyledonous plant species are transformable and regenerable such that whole plants containing and expressing desired genes under regulatory control of the promoter molecules according to the invention may be obtained. As is known to those of skill in the art, expression in transformed plants may be tissue specific and/or specific to certain developmental stages. Truncated promoter selection and structural gene selection are other parameters which may be optimized to achieve desired plant expression or inhibition as is known to those of skill in the art and taught herein.

The following is a non-limiting general overview of Molecular biology techniques which may be used in performing the methods of the invention.

Promoters

The constructs, promoters or control systems used in the methods of the invention may include a tissue specific promoter, an inducible promoter or a constitutive promoter.

A large number of suitable promoter systems are available. For example one constitutive promoter useful for the invention is the cauliflower mosaic virus (CaMV) 35S. It has been shown to be highly active in many plant organs and during many stages of development when integrated into the genome of transgenic plants including tobacco and petunia, and has been shown to confer expression in protoplasts of both dicots and monocots.

Organ-specific promoters are also well known. For example, the E8 promoter is only transcriptionally activated during tomato fruit ripening, and can be used to target gene expression in ripening tomato fruit (Deikman and Fischer, *EMBO J.* (1988) 7:3315; Giovannoni et al., *The Plant Cell* (1989) 1:53). The activity of the E8 promoter is not limited to tomato fruit, but is thought to be compatible with any system wherein ethylene activates biological processes. Similarly the Lipoxegenase ("the LOX gene") is a fruit specific promoter.

Other fruit specific promoters are the 1.45 promoter fragment disclosed in Bird, et al., *Plant Mol. Bio.,* pp 651–663(1988) and the polygalacturonase promoter from tomato disclosed in U.S. Pat. No. 5,413,937 to Bridges et al. Leaf specific promoters include as the AS-1 promoter disclosed in U.S. Pat. No. 5,256,558 to Coruzzi and the RBCS-3A promoter isolated from pea the RBCS-3A gene disclosed in U.S. Pat. No. 5,023,179 to Lam et al.

And finally root specific promoters include the Cam 35 S promoter disclosed in U.S. Pat. No. 391,725 to Coruzzi et al; the RB7 promoter disclosed in U.S. Pat. No. 5,459,252 to Conking et al and the promoter isolated from Brassica napus disclosed in U.S. Pat. No. 5,401,836 to Bazczynski et al. which give root specific expression.

Other examples of promoters include maternal tissue promoters such as seed coat, pericarp and ovule. Promoters highly expressed early in endosperm development are most effective in this application. Of particular interest is the promoter from the a' subunit of the soybean β-conglycinin gene [Walling et al., *Proc. Natl. Acad. Sci. USA* 83:2123–2127 (1986)] which is expressed early in seed development in the endosperm and the embryo.

Further seed specific promoters include the Napin promoter described in U.S. Pat. No. 5,110,728 to Calgene, which describes and discloses the use of the napin promoter in directing the expression to seed tissue of an acyl carrier protein to enhance seed oil production; the DC3 promoter from carrots which is early to mid embryo specific and is disclosed at *Plant Physiology,* Oct. 1992 100(2) p. 576–581, "Hormonal and Environmental Regulation of the Carrot Lea-class Gene Dc 3, and *Plant Mol. Biol., April* 1992, 18(6) p. 1049–1063, "Transcriptional Regulation of a Seed Specific Carrot Gene, DC 8": the phaseolin promoter described in U.S. Pat. No. 5,504,200 to Mycogen which discloses the gene sequence and regulatory regions for phaseolin, a protein isolated from *P. vulgaris* which is expressed only while the seed is developing within the pod, and only in tissues involved in seed generation.

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, Phil, *Trans. R. Soc. London* (1986) B314–343. mRNAs are first isolated to obtain suitable probes for retrieval of the appropriate genomic sequence which retains the presence of the natively associated control sequences. An example of the use of techniques to obtain the cDNA associated with mRNA specific to avocado fruit is found in Christoffersen et al., *Plant Molecular Biology* (1984) 3:385. Briefly, mRNA was isolated from ripening avocado fruit and used to make a cDNA library. Clones in the library were identified that hybridized with labeled RNA isolated from ripening avocado fruit, but that did not hybridize with labeled RNAs isolated from unripe avocado fruit. Many of these clones represent mRNAs encoded by genes that are transcriptionally activated at the onset of avocado fruit ripening.

Another very important method that can be used to identify cell type specific promoters that allow even to identification of genes expressed in a single cell is enhancer detection (O'Kane, C., and Gehring, W. J. (1987), "Detection in situ of genomic regulatory elements in Drosophila", *Proc. Natl. Acad. Sci. USA,* 84, 9123–9127). This method was first developed in Drosophila and rapidly adapted to mice and plants (Wilson, C., Pearson, R. K., Bellen, H. J., O'Kane, C. J., Grossniklaus, U., and Gehring, W. J. (1989), "P-element-mediated enhancer detection: an efficient method for isolating and characterizing developmentally regulated genes in Drosophila", *Genes & Dev.,* 3, 1301–1313; Skarnes, W. C. (1990), "Entrapment vectors: a new tool for mammalian genetics", *Biotechnology,* 8, 827–831; Topping, J. F., Wei, W., and Lindsey, K. (1991), "Functional tagging of regulatory elements in the plant genome", *Development,* 112, 1009–1019; Sundaresan, V., Springer, P. S., Volpe, T., Haward, S., Jones, J. D. G., Dean, C., Ma, H., and Martienssen, R. A., (1995), "Patterns of gene action in plant development revealed by enhancer trap and gene trap transposable elements", *Genes & Dev.,* 9, 1797–1810).

The promoter used in the method of the invention may be an inducible promoter. An inducible promoter is a promoter that is capable of directly or indirectly activating transcription of a DNA sequence in response to an inducer. In the absence of an inducer, the DNA sequence will not be transcribed. Typically, the protein factor that binds specifically to an inducible promoter to activate transcription is present in an inactive form which is then directly or indirectly converted to the active form by the inducer. The inducer may be a chemical agent such as a protein, metabolite (sugar, alcohol etc.), a growth regulator, herbicide, or a phenolic compound or a physiological stress imposed directly by heat, salt, toxic elements etc. or indirectly through the action of a pathogen or disease agent such as a virus. A plant cell containing an inducible promoter may be exposed to an inducer by externally applying the inducer to the cell such as by spraying, watering, heating, or similar methods. Examples of inducible promoters include the inducible 70 kd heat shock promoter of D. melanogaster (Freeling, M., Bennet, D. C., Maize ADN 1, *Ann. Rev. of Genetics,* 19:297–323) and the alcohol dehydrogenase promoter which is induced by ethanol (Nagao, R. T., et al., Miflin, B. J., Ed. Oxford Surveys of Plant Molecular and Cell Biology, Vol. 3, p. 384 –438, Oxford University Press, Oxford 1986) or the Lex A promoter which is triggered with chemical treatment and is available through Ligand pharmaceuticals. The inducible promoter may be in an induced state throughout seed formation or at least for a period which corresponds to the transcription of the DNA sequence of the recombinant DNA molecules(s).

Another example of an inducible promoter is the chemically inducible gene promoter sequence isolated from a 27 kd subunit of the maize glutathione-S-transferase (GST II) gene. Two of the inducers for this promoter are N,N-diallyl-2,2-dichloroacetamide (common name: dichloramid) or benzyl-=2-chloro-4-(trifluoromethyl)-5-thiazolecarboxylate (common name: flurazole). In addition, a number of other potential inducers may be used with this promoter as described in published PCT Application No. PCT/GB90/00110 by ICI.

Another example of an inducible promoter is the light inducible chlorophyll a/b binding protein (CAB) promoter, also described in published PCT Application No. PCT/GB90/00110 by ICI.

Inducible promoters have also been described in published Application No. EP89/103888.7 by Ciba-Geigy. In this application, a number of inducible promoters are identified, including the PR protein genes, especially the tobacco PR protein genes, such as PR-1a, PR-1b, PR-1c, PR-1, PR-A, PR-S, the cucumber chitinase gene, and the acidic and basic tobacco beta-1,3-glucanase genes. There are numerous potential inducers for these promoters, as described in Application No. EP89/103888.7.

The preferred promoters may be used in conjunction with naturally occurring flanking coding or transcribed sequences of the seed specific Polycomb genes or with any other coding or transcribed sequence that is critical to Polycomb formation and/or function.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant critical to seed specific Polycomb formation and/or function.

Additionally, regions of one promoter may be joined to regions from a different promoter in order to obtain the desired promoter activity resulting in a chimeric promoter. Synthetic promoters which regulate gene expression may also be used. The expression system may be further optimized by employing supplemental elements such as transcription terminators and/or enhancer elements.

Other Regulatory Elements

In addition to a promoter sequence, an expression cassette or construct should also contain a transcription termination region downstream of the structural gene to provide for efficient termination. The termination region or polyadenylation signal may be obtained from the same gene as the promoter sequence or may be obtained from different genes. Polyadenylation sequences include, but are not limited to the Agrobacterium octopine synthase signal (Gielen et al., *EMBO J.* (1984) 3:835–846) or the nopaline synthase signal (Depicker et al., *Mol. and Appl. Genet.* (1982) 1:561–573).

Marker Genes

Recombinant DNA molecules containing any of the DNA sequences and promoters described herein may additionally contain selection marker genes which encode a selection gene product which confer on a plant cell resistance to a chemical agent or physiological stress, or confers a distinguishable phenotypic characteristic to the cells such that plant cells transformed with the recombinant DNA molecule may be easily selected using a selective agent. One such selection marker gene is neomycin phosphotransferase (NPT II) which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis in RNA from the tissue of the transformed plant. Polymerase chain reactions are also used to identify the presence of a transgene or expression using reverse transcriptase PCR amplification to monitor expression and PCR on genomic DNA. Other commonly used selection markers include the ampicillin resistance gene, the tetracycline resistance and the hygromycin resistance gene. Transformed plant cells thus selected can be induced to differentiate into plant structures which will eventually yield whole plants. It is to be understood that a selection marker gene may also be native to a plant.

Transformation

A recombinant DNA molecule whether designed to inhibit expression or to provide for expression containing any of the DNA sequences and/or promoters described herein may be integrated into the genome of a plant by first introducing a recombinant DNA molecule into a plant cell by any one of a variety of known methods. Preferably the recombinant DNA molecule(s) are inserted into a suitable vector and the vector is used to introduce the recombinant DNA molecule into a plant cell.

The use of Cauliflower Mosaic Virus (CaMV) (Howell, S. H., et al, 1980, *Science,* 208:1265) and gemini viruses (Goodman, R. M., 1981, *J. Gen Virol.* 54:9) as vectors has been suggested but by far the greatest reported successes have been with Agrobacteria sp. (Horsch, R. B., et al, 1985, *Science* 227:1229–1231).

Methods for the use of Agrobacterium based transformation systems have now been described for many different species. Generally strains of bacteria are used that harbor modified versions of the naturally occurring Ti plasmid such that DNA is transferred to the host plant without the subsequent formation of tumors. These methods involve the insertion within the borders of the Ti plasmid the DNA to be inserted into the plant genome linked to a selection marker gene to facilitate selection of transformed cells. Bacteria and plant tissues are cultured together to allow transfer of foreign DNA into plant cells then transformed plants are regenerated on selection media. Any number of different organs and tissues can serve as targets from Agrobacterium mediated transformation as described specifically for members of the Brassicaceae. These include thin cell layers (Charest, P. J., et al, 1988, *Theor. Appl. Genet.* 75:438–444), hypocotyls (DeBlock, M., et al, 1989, *Plant Physiol.* 91:694–701), leaf discs (Feldman, K. A., and Marks, M. D., 1986, *Plant Sci.* 47:63–69), stems (Fry J., et al, 1987, *Plant Cell Repts.* 6:321–325), cotyledons (Moloney M. M., et al, 1989, *Plant Cell Repts.* 8:238–242) and embryoids (Neuhaus, G., et al, 1987, *Theor. Appl. Genet.* 75:30–36). It is understood, however, that it may be desirable in some crops to choose a different tissue or method of transformation.

Other methods that have been employed for introducing recombinant molecules into plant cells involve mechanical means such as direct DNA uptake, liposomes, electroporation (Guerche, P. et al, 1987, *Plant Science* 52:111–116) and micro-injection (Neuhaus, G., et al, 1987, *Theor. Appl. Genet.* 75:30–36). The possibility of using microprojectiles and a gun or other device to force small metal particles coated with DNA into cells has also received considerable attention (Klein, T. M. et al., 1987, *Nature* 327:70–73).

It is often desirable to have the DNA sequence in homozygous state which may require more than one transformation event to create a parental line, requiring transformation with a first and second recombinant DNA molecule both of which encode the same gene product. It is further contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant molecules are linked or located on the same chromosome, and then selecting from the progeny of the cross, plants containing both DNA sequences or recombinant DNA molecules.

Expression of recombinant DNA molecules containing the DNA sequences and promoters described herein in transformed plant cells may be monitored using Northern blot techniques and/or Southern blot techniques known to those of skill in the art.

A large number of plants have been shown capable of regeneration from transformed individual cells to obtain transgenic whole plants. For example, regeneration has been shown for dicots as follows: apple, Malus pumila (James et al., *Plant Cell Reports* (1989) 7:658); blackberry, Rubus, Blackberry/raspberry hybrid, Rubus, red raspberry, Rubus (Graham et al., *Plant Cell, Tissue and Organ Culture* (1990) 20:35); carrot, Daucus carota (Thomas et al., *Plant Cell Reports* (1989) 8:354; Wurtele and Bulka, *Plant Science* (1989) 61:253); cauliflower, Brassica oleracea (Srivastava et al., *Plant Cell Reports* (1988) 7:504); celery, Apium graveolens (Catlin et al., *Plant Cell Reports* (1988) 7:100); cucumber, Cucumis sativus (Trulson et al., *Theor. Appl. Genet.* (1986) 73:11); eggplant, Solanum melonoena (Guri and Sink, *J. Plant Physiol.* (1988) 133:52) lettuce, Lactuca sativa (Michelmore et al., *Plant Cell Reports* (1987) 6:439); potato, Solanum tuberosum (Sheerman and Bevan, *Plant Cell Reports* (1988) 7:13); rape, Brassica napus (Radke et al., *Theor. Appl. Genet.* (1988) 75:685; Moloney et al., *Plant Cell Reports* (1989) 8:238); soybean (wild), Glycine canescens (Rech et al., *Plant Cell Reports* (1989) 8:33); strawberry, Fragaria x ananassa (Nehra et al., *Plant Cell Reports* (1990) 9:10;

tomato, Lycopersicon esculentum (McCormick et al., *Plant Cell Reports* (1986) 5:81); walnut, Juglans regia (McGranahan et al., *Plant Cell Reports* (1990) 8:512); melon, Cucumis melo (Fang et al., 86th Annual Meeting of the American Society for Horticultural Science *Hort. Science* (1989) 24:89); grape, Vitis vinifera (Colby et al., Symposium on Plant Gene Transfer, UCLA Symposia on Molecular and Cellular Biology *J Cell Biochem Suppl* (1989) 13D:255; mango, Mangifera indica (Mathews, et al., symposium on Plant Gene Transfer, UCLA Symposia on Molecular and Cellular Biology *J Cell Biochem Suppl* (1989) 13D:264);

and for the following monocots: rice, Oryza sativa (Shimamoto et al., *Nature* (1989) 338:274); rye, Secale cereale (de la Pena et al., *Nature* (1987) 325:274); maize, (Rhodes et al., *Science* (1988) 240:204).

In addition regeneration of whole plants from cells (not necessarily transformed) has been observed in apricot, Prunus armeniaca (Pieterse, *Plant Cell Tissue and Organ Culture* (1989) 19:175); asparagus, Asparagus officinalis (Elmer et al., *J. Amer. Soc. Hort. Sci.* (1989) 114:1019);

Banana, hybrid Musa (Escalant and Teisson, *Plant Cell Reports* (1989) 7:665); bean, Phaseolus vulgaris (McClean and Grafton, *Plant Science* (1989) 60:117); cherry, hybrid Prunus (Ochatt et al., *Plant Cell Reports* (1988) 7:393); grape, Vitis vinifera (Matsuta and Hirabayashi, *Plant Cell Reports*, (1989) 7:684; mango, Mangifera indica (DeWald et al., *J Amer Soc Hort Sci* (1989) 114:712); melon, Cucumis melo (Moreno et al., *Plant Sci letters* (1985) 34:195); ochra, Abelmoschus esculentus (Roy and Mangat, *Plant Science* (1989) 60:77; Dirks and van Buggenum, *Plant Cell Reports* (1989) 7:626); onion, hybrid Allium (Lu et al., *Plant Cell Reports* (1989) 7:696); orange, Citrus sinensis (Hidaka and Kajikura, *Scientia Horiculturae* (1988) 34:85); papaya, Carrica papaya (Litz and Conover, *Plant Sci Letters* (1982) 26:153); peach, *Prunus persica* and plum, *Prunus domestica* (Mante et al., *Plant Cell Tissue and Organ Culture* (989) 19:1); pear, Pyrus communis (Chevreau et al., *Plant Cell Reports* (1988) 7:688; Ochatt and Power, *Plant Cell Reports* (1989) 7:587); pineapple, Ananas comosus (DeWald et al., *Plant Cell Reports* (1988) 7:535);

watermelon, Citrullus vulgaris (Srivastava et al., *Plant Cell Reports* (1989) 8:300); wheat, Triticum aestivum (Redway et al., *Plant Cell Reports* (1990) 8:714).

The regenerated plant are transferred to standard soil conditions and cultivated in a conventional manner.

After the expression or inhibition cassette is stably incorporated into regenerated transgenic plants, it can be transferred to other plants by sexual crossing. Any of a number of standard breeding techniques can be used, depending upon the species to be crossed.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

As indicated above, it may be desirable to produce plant lines which are homozygous for a particular gene. In some species this is accomplished rather easily by the use of anther culture or isolated microspore culture. This is especially true for the oil seed crop Brassica napus (Keller and Armstrong, Z. flanzenzucht 80:100–108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

Creation of homozygous parental lines makes possible the production of hybrid plants and seeds which will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The following examples serve to better illustrate the invention described herein and are not intended to limit the invention in any way.

EXAMPLES

Example 1

In a screen for Arabidopsis mutations affecting the gametophyte generation (J. Moore, W. Gagliano, J-P. Vielle Calzada, U. Grossniklaus, unpublished.), we identified a mutant in which self-fertilization of a heterozygote produces 50% aborted seeds that collapse, accumulate anthocyanin and do not germinate (FIG. 2A). This non-Mendelian 1:1 segregation of aborted to normal seeds is consistent with a gametophytic control of the defect, since half of the gametophytes receive the mutant allele in a heterozygote. Reciprocal crosses between mutants and wild type showed that heterozygous embryos abort if the mutant allele is derived from the female (FIG. 2B), but develop normally if it is introduced through the male (FIG. 2C; Table 1).

TABLE 1

Seed phenotype of reciprocal crosses between mea and wild type.

Green or dry siliques resulting from self pollination or out-crosses to Columbia (Col) were opened and the seeds classified as unfertilized ovules, normal or aborted seeds. N (seeds), number of seeds scored.

|  | mea selfed | mea × Col | Col × mea |
|---|---|---|---|
| unfertilized | 12% | 13% | 11% |
| normal | 42% | 43% | 88% |
| aborted | 46% | 44% | 1% |
| N (seeds) | 1461 | 770 | 514 |

Because reciprocal crosses confer different phenotypes and embryos derived from mutant eggs abort irrespective of the paternal contribution, this mutant displays maternal effect embryo lethality. In flowering plants, maternal effects can be controlled by either the female gametophyte (L. A. Castle et al., *Mol. Gen. Genet.* 241, 504 (1993); N. Ohad et al., *Proc. Natl. Acad. Sci. USA* 93, 5319 (1996); A. M. Chaudhury et al., *Proc Natl. Acad. Sci. USA* 94, 4223 (1997)) or the sporophytic tissue of the plant (S. Ray, T. Golden, A. Ray, *Dev. Biol.* 180, 365 (1996); Colombo et al., *Plant Cell* 9, 703 (1997)). We named this gametophytic maternal effect mutant medea (mea) because the genotype of the female gametophyte determines whether the embryo survives or dies (Euripides (431 BC). Jason's mistress Medea kills her two children to punish him for arranging a marriage with the daughter of king Creon).

Fertilization of egg and central cell leads to the formation of two products, the diploid zygote and the triploid primary endosperm nucleus. Endosperm resulting from a cross between a mea-1 female and wild type carries two mutant mea-1 and one wild type MEA allele. Hence, seed abortion could be caused by a mutation in a dosage sensitive gene required for endosperm development. To test this hypothesis, we introduced additional wild type MEA copies: In a cross between a mea-1 heterozygote and a wild type tetraploid male, half of the developing seeds abort (Table 2) and the mutant mea-1 allele is not recovered in the progeny (0/41). In control crosses seeds rarely abort (Table 2), and paternal mea-1 alleles are transmitted to half the offspring (64).

TABLE 2

Seed phenotype of reciprocal crosses between mea and a tetraploid

Green or dry siliques resulting from crosses with a tetraploid or self pollination were opened and the seeds classified as unfertilized ovules, normal or aborted seeds. In crosses involving tetraploids fertility is reduced because of a large fraction of unfertilized ovules (J. H. van der Veen and H. Blankenstijn-de Vries, Arabidopsis Inf. Serv., 10, 11 (1973)). The relative increase in unfertilized ovules in the "Col × 4n" cross is due to longer siliques and a larger number of ovules per silique in Col plants (Col: 65.1 +/− 6.4; mea-1: 39.7 +/− 5.9; 4n: 43.6 +/− 3.2). Pollen viability in tetraploids is reduced such that only ovules at the top of the silique get fertilized. The average number of seeds per silique initiating development is similar (Col: 17.9 +/− 2.1; mea-1: 22.1 +/− 5.9; 4n: 26.1 +/− 4.4). The "normal" class includes brown, regularly shaped seeds that are smaller than wild type and are common in crosses involving plants of different ploidy. They do not show the collapsed, black mea phenotype. N (seeds), number of seeds scored.

|  | mea-1 × 4n | Col × 4n | 4n × mea-1 | 4n × Col | 4n selfed |
|---|---|---|---|---|---|
| unfertilized | 45% | 72% | 37% | 40% | 46% |
| normal | 26% | 27% | 59% | 54% | 52% |
| aborted | 29% | 1% | 4% | 6% | 2% |
| N (seeds) | 437 | 587 | 1155 | 696 | 1489 |

These results suggest that seed abortion in mea plants is not caused by haplo-insufficiency in the endosperm. An additional paternal wild type MEA allele is unable to rescue maternal effect lethality. Thus, mea either affects a maternally produced cytoplasmic factor deposited in egg and/or central cell, or disrupts an imprinted gene expressed from the maternal allele. Similar results were obtained using mea-2, (data not shown), a second allele of mea-1. The mea-2 differs from wild-type at amino acid 581 (Asp to Glu) and 582 (Glu to Ser). Since both alleles show similar genetic and phenotypic behavior, they appear to be of the same allelic strength.

Example 2

Although desiccated mea seeds do not germinate (0/~1600=0%), they can do so if precociously germinated on nutritive medium before desiccation (27/172=16%). This finding suggests that the initiation of desiccation program during seed maturation leads to seed abortion rather than a failure to form embryo or endosperm. To determine the developmental potential of embryos derived from mea eggs (hereafter referred to as mea embryos) before desiccation, they were excised and cultured in vitro (data not shown). These embryos continue to grow and eventually form seedlings although many of them show morphological defects. Seedlings rescued in culture or through precocious germination displayed variable phenotypes ranging from wild type to highly abnormal lethal seedlings. Abnormalities include the absence of root or shoot, pigmentation defects, production of callus-like structures, variable cotyledon number and aberrant vegetative growth. Because some wild type seedlings are formed mea does not appear to affect embryo morphogenesis but rather the abnormal phenotype of some mea seedlings is an indirect effect depending on the degree of desiccation and accompanying necrosis at the time of precocious germination or embryo rescue in culture. Despite the seedling abnormalities affecting a portion of the progeny, about half of the mea seedlings (30/64=47%) will grow into adult plants producing flowers. In this manner we were able to produce mea homozygotes which carried exclusively mutant mea alleles. The vegetative and reproductive phase of these homozygous mutants is normal and non obvious defects were observed. After possible initial abnormalities, the plants produce wild type looking rosette and cauline leaves, inflorescence and flowers but, as expected, their siliques contain 100% aborted seeds. These results strongly suggest that mea is not required for post-embryonic growth and development and specifically affects seed development.

Example 3

Figure 3:
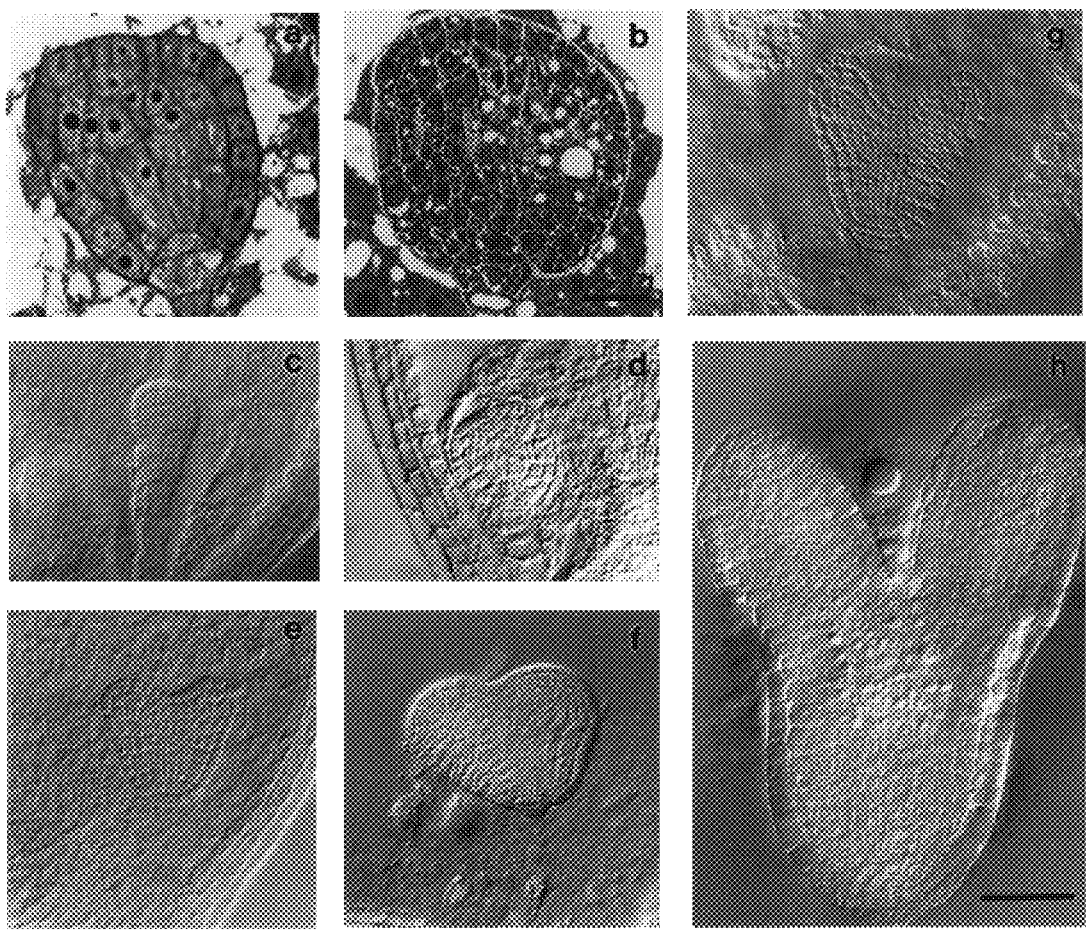

Few maternal effect mutants have been described in plants and the molecular and genetic basis of their function is unknown. To characterize the mea-1 phenotype, we compared the morphology of developing wild type and mea seeds in cleared or sectioned specimens (For whole-mount specimens siliques were fixed in 3:1 ethanol:acetic acid for 2 hours, and cleared in Hoyer's as described (T. Berleth, and G. Jürgens, Dev., 118, 575 (1993)). For sectioned material, siliques were fixed in 30% glutaraldehyde for 2 hours, rinsed in 50 mM cacodylate buffer, and postfixed in 2% $OsO_4$. After dehydration in an ethanol series, specimens were embedded in Spurr's media as described (A. R. Spurr, J. Ultrastruct. Res., 26, 31 (1969)). Seeds were observed using bright field and DIC optics). During early stages of embryogenesis the development of mea-1 embryos is indistinguishable from wild type (data not shown). Differences between wild type and mea-1 embryos were observed at the late globular stage (FIG. 3, A to D). Due to abnormal cell proliferation, globular mea-1 embryos enlarge but remain radially symmetrical. When wild type embryos reach the mid heart to late heart stage, sibling mea-1 embryos are still globular and contain small vacuolated cells with curvilinear cell walls and sometimes irregular patterns of division in the ground tissue and procambium (FIG. 3, A & B). The suspensor and hypophysis are normal, and cotyledons initiate synchronously as in wild type. Thus, despite increased proliferation and occasional irregular division patterns, morphogenetic progression is normal. However, since each stage is prolonged and presumably includes more division cycles, morphogenesis is delayed. As a consequence, giant mid heart to late heart mea-1 embryos (FIG. 3, E to H) are present in siliques containing wild type embryos at the late torpedo or cotyledonary stages. mea-1 embryos have supernumerary cell layers confirming increased cell proliferation (mea-1: 19.6+/−1.1; wild type: 13.0+/−0.9). When wild type siblings are fully differentiated, most mea-1 embryos have reached the late heart stage (FIG. 3, G & H) and are approximately 10 times larger than corresponding wild type embryos. They degenerate during desiccation. These results suggest that mea controls cell proliferation during embryogenesis without affecting morphogenetic progression, which is normal although slow.

Endosperm development in mea-1 seeds was characterized in sectioned material (data not shown). At early stages, mea-1 endosperm is indistinguishable from wild type. As cellularization begins in wild type seeds at the transition from the globular to the heart stage, no signs of cellularization were observed in sibling mea-1 seeds. mea-1 endosperm is characterized by a reduction of the rate at which free nuclear divisions take place but the characteristic distribution of endosperm nuclei is as in wild type. Partial cellularization occurs at the micropyle when mea-1 embryos reach the late heart stage in desiccating seeds, but due to fewer free nuclear divisions most of the central cell is devoid of nuclei. Thus, in mea-1 seeds the development of both fertilization products is delayed but morphogenesis proceeds normally, and it appears that the embryo shows increased proliferation at the expense of the endosperm.

Example 4

To determine the function of the MEA wild type product we investigated whether mea-1 is a gain-of-function or loss-of-function mutation. Since dominance and recessiveness are defined as an interaction of two alleles in the same organism, this question is difficult to address for gametophytically required genes. We introduced mea-1 into a tetraploid background which produces diploid gametophytes carrying either none, one or two mea-1 alleles (mea was crossed as a male to a tetraploid, and triploid progeny carrying mea was allowed to self-fertilize. Triploid plants produce few seeds which include diploids, triploids, aneuploids and at a low frequency tetraploids. Most aneuploid seeds are small (G. Röbbelen and F. J. Kribben, Arabidopsis Inf. Serv., 3, 16 (1966)), whereas tetraploid seeds are larger than wild type. Large seeds were selected and tetraploid plants identified based on morphology (J. Bouharmont and F. Macé, Can. J. Genet. Cytol., 14, 257 (1972)), reduced seed set and altered segregation pattern of mea seeds. Their tetraploid nature was verified by chromosome counts of DAPI stained root tip preparations as described (J. Maluszynska and J. S. Heslop-Harrison, Ann. Bot., 71, 479 (1993)). Inheritance of seed abortion and kanamycin resistance linked to mea-1 was analyzed. Since tetraploids carrying one (simplex) or two (duplex) mutant alleles could have been recovered, we considered models for both possibilities with mea-1 being either recessive or dominant (Table 3).

TABLE 3

Segregation of embryo lethality and kanamycin resistance in a 4n mea line

The tetraploid nature of this plant was confirmed at the cytogenetic level (data not shown). Dry siliques were opened and their seeds classified as normal or aborted seeds displaying the mea phenotype. The progeny of this plant was tested for sensitivity ($Kan^S$) or resistance to kanamycin ($Kan^R$) linked to mea-1. Expected values of the two phenotypes scored are given for four different models [(1) to (4)]. For the calculation of expected progeny classes, a spontaneous embryo abortion rate of 1.5% as determined for the parental tetraploid was included. The coefficient of double reduction was taken as c = 0.1 (J. H. van der Veen and H. Blankenstijn-de Vries, Arabidopsis Inf. Serv., 10, 11 (1973)).

|  | aborted | normal | $X^2$ | $Kan^R$ | $Kan^S$ | $X^2$ |
|---|---|---|---|---|---|---|
| Observed | 17 | 182 |  | 247 | 84 |  |
| (1) Simplex, mea recessive | 15 | 184 | 0.29 | 237 | 94 | 1.48 |
| (2) Duplex, mea recessive | 48 | 151 | 26.4 | 314 | 17 | 278.4 |
| (3) Simplex, mea dominant | 98 | 101 | 131.9 | 155 | 176 | 102.7 |
| (4) Duplex, mea dominant | 161 | 38 | 674.5 | 265 | 66 | 6.1 |

Our data are consistent with a simplex recessive model ($X^2 < \chi^2_{0.05[1]} = 3.84$). The recessive nature of mea-1 is confirmed by the high transmission frequency of kanamycin resistance (247/331=75%). If mea-1 were dominant it would be exclusively transmitted through pollen at a frequency of about 47% in a simplex tetraploid (Transmission was calculated by taking the coefficient of double reduction (the frequency at which the alleles of two sister chromatids are recovered in the same gamete) c=0.1 as previously estimated for this chromosomal region. (J. H. van der Veen and H. Blankenstijn-de Vries, Arabidopsis Inf. Serv., 10, 11 (1973)). Similar results were obtained with a tetraploid plant carrying the mea-2 allele. These results strongly suggest that mea-1 and mea-2 are a loss-of-function mutation. Thus, the wild type function of MEA is to restrict cell proliferation during embryogenesis.

Example 5

To gain insight into the molecular nature of the mea maternal effect phenotype, we cloned and characterized the MEA gene. mea-1 was isolated in an insertional mutagenesis screen using derivatives of the maize Ac/Ds transposon system (V. Sundaresan et al., Genes & Dev., 9, 1797 (1995); P. S. Springer, W. R. McCombie, V. Sundaresan, R. Martienssen, Science, 268, 877 (1995)). Two findings suggested that mea-1 is molecularly tagged: First, mea-1 and the Ds element co-segregated and no recombination could be detected between them. Second, the mutation is unstable in the presence of Ac transposase and large revertant sectors could be identified in plants heterozygous for both mea-1 and Ac. We used genomic fragments flanking the Ds element to screen a cDNA library (Genomic DNA flanking the mea-1 Ds insertion was isolated by TAIL-PCR (Yu et al., Nature, 378, 595 (1995)). Three nested primers for both the 5' and 3' end of Ds were used in consecutive rounds of PCR in combination with either the AD1 or AD2 primer (Yu et al., Nature, 378, 595 (1995)) PCR conditions were as in (Yu et al., Nature, 378, 595 (1995)) with minor modifications: The primary PCR reaction was incubated at 95° C. for 2 min. before initiating the first 5 high stringency cycles. In the secondary reaction, 15 instead of 12 supercycles, and in the tertiary reaction 25 instead of 20 low stringency cycles were performed. The nested Ds primers were: Ds5-1 (5'-CCGTTTACCGTTTTGTATATCCCG-3') SEQ ID NO:5, Ds5-2 (5'-CGTTCCGTTTTCGTTTTTTACC-3') SEQ ID NO:6, Ds5-3 (5'-GGTCGGTACGGCAATTCTCCC-3')SEQ ID NO:7, Ds3-1 (5'-CGATTACCGTATTTATCCCGTTCG-3') SEQ ID NO:8, Ds3-2 (5'-CCGGTATATCCCGTTTTCG-3') SEQ ID NO:9, Ds3-3 (5'-GTTACCGACCGTTTTCATCC-3') SEQ ID NO:10. Tertiary or secondary products were subcloned into the pTAdvantage vector (Clontech). 8×10$^5$ phages from a flower cDNA library (D. Weigel et al., Cell, 69, 843 (1992) were screened using the EcoRI fragment of clone mah17 (3' TAIL-PCR subclone) as a probe. A single cDNA phage was isolated. The plasmid excised using the ExAssist helper phage and sequenced. The cDNA contained a poly-A tail but was not full length. The 5' end was isolated by 5' RACE PCR: 1 mg of total RNA from young siliques was reverse transcribed using 2.5 pmoles of meaAS3 (5'-CCAGCAGTTCCATCATTC-3') SEQ ID NO:11 in a 20 $\mu$l reaction containing 1×PCR buffer (GIBCO-BRL), 2.5 mM MgCl$_2$, 0.5 mM each dNTP, 10 mM DTT and 200 units of Superscript reverse transcriptase (GIBCO-BRL) by incubating at 42° C. for 1 hour. Following heat inactivation at 70° C. for 20 min., the sample was treated with 2 units of RNAse H (GIBCO-BRL) at 37° C. for 30 min. The cDNA was purified using the PCR Purification kit (Perkin Elmer/Cetus). 1/5 of the sample was treated with 15 units of terminal deoxynucleotidyl transferase (GIBCO-BRL) in 10 mM Tris pH 8.4, 25 mM KCl, 1.5 mM MgCl$_2$ and 0.2 mM dCTP at 37° C. for 10 min., followed by heat inactivation at 65° C. The first round of PCR was performed in 1×PCR buffer (Perkin Elmer), 2 mM MgCl$_2$, 0.2 mM each dNTP, 1 unit of Taq polymerase (Perkin-Elmer/Cetus), and 20 pmoles each primer, 5RACE Abridged Adapter Primer (5RACEAAP, GIBCO-BRL) and meaAS4 (5'-GTCCGAAACATCCACTTCG-3') SEQ ID NO:12 for 35 cycles at an annealing temperature of 55° C. 1/20 of the product was used in the second round of PCR performed under the same conditions but with the primers Abridged Universal Adapter Primer (AUAP, GIBCO-BRL) and meaAS5 (5'-CGACCAGATCATCCAAACCATAG-3') SEQ ID NO:13. The PCR products were ligated into the pTAdvantage vector (Clontech); four subclones were sequenced to derive a composite cDNA sequence). Sequencing of a MEA cDNA (FIG. 4A) showed that it is similar to Enhancer of zeste [E(z)], a Drosophila protein best known for its involvement in the regulation of homeotic genes. The highest similarity between the two proteins (55% identity) is found at the C-terminus (FIG. 4B), in the SET domain, which was named after the three founding members of the family in Drosophila, Suppressor of variegation 3-9 [Su(var) 3-9], E(z), and trithorax (trx) (FIG. 4C) (B. Tschiersch et al., EMBO J., 13, 3822 (1994); A. M. Mazo, D-H. Huang, B. A. Mozer, I. B. David, Proc. Natl. Acad. Sci. USA, 87, 2112 (1990); Jones, R. S. et al., "The Drosophila Polycomb-Group Gene Enhancer of zeste Contains a Region with Sequence Similarity to trithorax", Mol. Cell. Biol. 13, 6357–6388 (1993). Although the function of the SET domain is unknown, members of this family are thought to regulate gene expression by associating with chromatin at specific sites thereby controlling access to transcription factors (V. Orlando and R. Paro, Curr. Opin. Genet. Dev., 5, 174 (1995); V. Pirrotta, Curr. Opin. Genet. Dev., 7, 249 (1997)). E(z) shows characteristics of both the trithorax group (trx-G) and Polycomb group (Pc-G) in Drosophila (LaJeunesse, D., et al., "E(z): a Polycomb group gene or a trithorax group gene?", Development, Vol. 122, 2189–2197 (1996)). Pc-G and trx-G proteins play an important role in the long-term activation and repression of homeotic genes in Drosophila, mice and plants (Simon, J., "Locking in stable states of gene expression: transcriptional control during Drosophila development", Curr Opin. Cell Biol. Vol. 7, 376–385(1995); Alkema et al., Nature, 374, 724 (1995); Yu et al., Nature, 378, 595 (1995); Goodrich, J., et al., "A Polycomb-group gene regulates homeotic gene expression in Arabidopsis", Nature 386, 44–51 (1997)). In addition, many of them show parent-of-origin-specific effects and regulate cell proliferation (Jones, R. S. et al., "The Drosophila Polycomb-Group Gene Enhancer of zeste Contains a Region with Sequence Similarity to trithorax", Mol. Cell. Biol. 13, 6357–6388 (1993); M. Gatti and B. S. Baker, Genes Dev. 3, 438 (1989); Phillips, M. D., et al., Genetics, Vol. 125, 91–101 (1990)). For instance, the human homologs of trx (All-1/Hrx) and E(z) (Enx-1) are involved in the control of lymphocyte proliferation (D. C. Tkachuk, S. Kohler, M. L. Cleary, Cell, 71, 869 (1992); Y. Gu et al., "The t(4;11) Chromosome Translocation of Human Acute Leukemias Fuses the ALL-1 Gene, Related to Drosophila trithorax, to the AF-4 Gene", Cell, Vol. 71, 701–708 (1992); O. Hobert, et al., "Interaction of Vav with ENX-1, a Putative Transcriptional Regulator of Homeobox Gene Expression", Mol. Cell. Biol. 16, 3066–3073 (1996)), and the C. elegans E(z) homolog MES-2 is required for the survival of the germline (E. E. Capowski, P. Martin, C. Garvin, S. Strome, Genetics, 129, 1061 (1991); R. Holdeman, S. Nehrt, S. Strome, "A Polycomb Group Gene is Essential for Viability of the Germline in C. elegans", personal communication). Whereas MEA controls cell proliferation, the plant E(z) homolog CURLY LEAF (CLF) regulates expression of floral homeotic genes (Goodrich, J., et al., "A Polycomb-group gene regulates homeotic gene expression in Arabidopsis", Nature 386, 44–51 (1997)) indicating that both functions of SET domain proteins have been conserved across kingdoms. MEA shares 43% identity with E(z) in the CXC domain, a cysteine-rich region N-terminal to the SET domain (FIG. 3B). The CXC domain and a five additional highly conserved cysteine residues (FIGS. 4 A & B) are unique to E(z) and its vertebrate and plant homologs (Goodrich, J., et al., "A Polycomb-group gene regulates homeotic gene expression in Arabidopsis", Nature 386, 44–51 (1997)); O. Hobert et al., Mech. Dev., 55, 171 (1996)). Although the function of these regions is unknown, they are required for E(z) activity (Carrington, E. A., et al., "The Drosophila Enhancer of zeste gene encodes a chromosomal protein: examination of wild-type and mutant protein distribution", Development, Vol. 122, 4073–4083 (1996)). The similarity to SET domain proteins suggests that MEA controls cell proliferation by regulating gene expression through modulating higher order chromatin structure.

The Ds element in mea-1 inserted N-terminal to residues of the SET domain that are invariant among the E(z) homologs (FIG. 4C). To confirm that the isolated gene corresponds to the mea mutation, we sequenced the region spanning the insertion site in 3 independently recovered revertants.

(Genomic DNA from Landsberg erecta was isolated wild type plants, plants heterozygous for the Ds allele mea-1, the mea-2 excision allele, and seedlings derived from 3 independent large revertant sectors was isolated according to (K. Edwards, C. Johnstone, C. Thompson, *Nucleic Acids Res.* 15, 1349 (1991). The junction fragments were amplified by PCR in 1×PCR buffer (Perkin/Elmer) containing 2 mM $MgCl_2$, 0.2 mM each dNTP, 1 unit of Taq DNA polymerase (Perkin-Elmer/Cetus), and 40 pmoles of each specific primer for 40 cycles at an annealing temperature of 55° C. The primers used were mea5-3 (5'-CGTAGCAGTTAGGTCTTGC-3') SEQ ID NO:14 and mea3-1 (5'-CGTCGACCCGTCAGGACTCTC-3') SEQ ID NO:15. For mea-1 DNA mea5-3 and mea3-1 were used in combination with primers Ds5-2 (5'-CGTTCCGTTTTCGTTTTTTACC-3') SEQ ID NO:5 and Ds3-2 (5'-CCGGTATATCCCGTTTTCG-3') SEQ ID NO:9. The PCR products were ligated into the pTAdvantage vector (Clontech); four to five subclones were sequenced for each derivative allele.)

Ds excisions usually create characteristic footprints, and phenotypic revertants should restore the open reading frame of the disrupted gene. In all three revertants the sequence was wild type (FIG. 4E), indicating a strong sequence constraint on this region of the SET domain. In the phenotypically mutant excision allele mea-2 a 7 base pair footprint remains introducing two stop codons (FIG. 4E). These results confirm that the mea phenotype is caused by a disruption of the SET domain protein.

To investigate the expression profile of the MEA transcript, we performed semi-quantitative RT-PCR analysis in floral tissues and developing siliques (FIG. 3D). (For RNA preparation, tissue from wild-type Landsberg erecta plants was harvested in liquid nitrogen. RNA from buds, unpollinated and pollinated carpels, and young siliques was prepared using the Trizol LS reagent (GIBCO-BRL). RNA from tissues high in starch content was prepared using the Qiagen RNeasy kit (Qiagen). For accurate sampling each silique was dissected and the stage to which embryogenesis had progressed was determined. For reverse transcription polymerase chain reaction (RT-PCR) 5 mg of total RNA were treated with 5 units of RNAse free DNAse in 1×PCR buffer (GIBCO-BRL) containing 2.5 mM $MgCl_2$. The DNAse was heat inactivated at 80° C. for 5 min., the samples extracted with phenol-chloroform-isoamyl alcohol (25:24:1) and ethanol precipitated. The RNA was reverse transcribed to cDNA using 5 pmoles of random hexamers (Pharmacia Biotech). 1 mg of total RNA from the different stages was reverse transcribed using 2.5 pmoles of meaAS3 (5'-CCAGCAGTTCCATCATTC-3') SEQ ID NO:11 in a 20 ml reaction containing 1×PCR buffer (GIBCO-BRL), 2.5 mM $MgCl_2$, 0.5 mM each dNTP, 10 mM DTT and 200 units of Superscript reverse transcriptase (GIBCO-BRL) by incubating at 42° C. for 1 hour. Following heat inactivation at 70° C. for 20 min., the sample was treated with 2 units of RNAse H (GIBCO-BRL) at 37° C. for 30 min. The cDNA was purified using the PCR Purification kit (Perkin Elmer/Cetus). 1/5 of the cDNA samples was used for the PCR amplification of MEA, whereas 1/10 of the samples was used to amplify the ACT11 and At2S2 transcripts (J. M. McDowell et al., *Genetics*, 142, 587 (1996); P. Guerche et al., *Plant Cell*, 2, 469 (1990)) which served as controls. PCR was performed in 1×PCR buffer (Perkin Elmer) containing 2 mM $MgCl_2$, 0.2 mM each dNTP, 1 unit of Taq DNA polymerase (Perkin-Elmer/Cetus), and 20 pmoles each gene specific primer for 30 cycles at an annealing temperature of 55° C. The primers used for amplification of MEA, ACT11 and At2S2, respectively, were as follows: meaS4 (5'-GCAGGACTATGGTTTGGATG-3') SEQ ID NO:16, meaAS6 (5'-CACCTTGAGGTAACAATGCTC-3') SEQ ID NO:17, Act11F (5'-AACTTTCAACACTCCTGCCATG-3') SEQ ID NO:18, Act11R (5'-CTGCAAGGTCCAAACGCAGA-3') SEQ ID NO:19, At2S2F (5'-GAGCCAGTTTGTGTTTGC-3') SEQ ID NO:20,At2S2R (5'-TAAGGAGGGAAGAAAGGG-3') SEQ ID NO:21).

MEA is not expressed at early stages of flower development during the early phase of megagametogenesis. MEA is first detectable in unpollinated siliques that contain maturing gametophytes indicating maternal expression. Subsequently, the transcript is present throughout the morphogenetic phase of embryogenesis and starts to disappear during seed maturation. These findings are consistent with MEA being either an unusually stable mRNA that is maternally deposited in egg and/or central cell and persists for two weeks throughout seed development, or that MEA is expressed both maternally and zygotically. Expression after fertilization would suggest that MEA expression is regulated by genomic imprinting since paternally provided copies cannot rescue embryo lethality.

Example 6

The regulation of cell proliferation and growth during seed development by MEA is under maternal control. Haig and Westoby proposed that parent-of-origin-specific effects evolved as a consequence of an intra-genomic conflict over the allocation of nutrients from the mother to its offspring (D. Haig and M. Westoby, *Am. Nat.*, 134, 147 (1989).

Although their theory is usually discussed with respect to imprinting it is equally applicable to other post-meiotically established differences such as a maternal effect of cytoplasmic nature. The intra-genomic conflict theory predicts that parentally controlled loci should influence the growth rate of the embryo, with paternally expressed genes promoting growth and maternally expressed ones tending to reduce it (D. Haig and M. Westoby, *Am. Nat.*, 134, 147 (1989)). Supporting evidence has been provided by studies on imprinted genes in mice and humans (D. Haig and C. Graham, *Cell*, 64, 1045 (1991); R. Jaenisch, *Trends Genet.*, 13, 323 (1997); W. Reik and E. R. Maher, *Trends Genet.*, 13, 330 (1997)) and from the manipulation of entire genomes in flowering plants (B-Y Lin, *Genetics*, 100, 475 (1982); V. Kermicle and M. Alleman, *Tr. Suppl.* 1, 9 (1990); D. Haig and M. Westerby, *Phi. Trans. Soc.*, Lond.). The mea mutant phenotype and its regulation is consistent with the parental conflict theory. Our findings suggest that similar molecular mechanisms operate in animals and plants to control cell proliferation and to mediate parent-of-origin-specific effects.

Example 7

The mea-1 and mea-2 mutants were evaluated for their ability to initiate seed development in the absence of fertilization. Seeds developing from mea-1 and mea-2 heterozygous plants that were emasculated were not green as seeds derived from a fertilization event but rather white indicating seed abortion and thus likely the result of autonomous development. Not all emasculated siliques were elongated and some did not contain any seed-like structures within them. Others contained between 2 and 18 white seeds in siliques that were opened one week after emasculation. The results are summarized in Table 4.

TABLE 4

| | | | |
|---|---|---|---|
| mea-1 | 47 white seeds | 224 undeveloped ovules | 6 siliques scored |
| mea-2 | 6 white seeds | 194 undeveloped ovules | 5 siliques scored |

In mea-2 many siliques may have been damaged during the emasculation. Therefore this may be an underestimate.

As can be seen from the foregoing the invention accomplishes at least all of its objectives.

What is claimed is:

1. A purified and isolated nucleotide sequence which encodes upon expression a regulatory protein characterized by the following:
   (a) is a Polycomb group member;
   (b) comprises a SET domain or a CXC domain or both;
   (c) regulates seed specific cell proliferation; and
said nucleotide sequence being capable of hybridizing under conditions of high stringency to SEQ ID NO:1.

2. The nucleotide sequence of claim 1 wherein said sequence is SEQ ID NO:1.

3. An expression construct comprising:
   a nucleotide sequence according to claim 1, operatively linked to a regulatory region capable of directing expression of a protein in a plant cell.

4. A vector capable of transforming or transfecting a host cell, said vector comprising an expression construct according to claim 3.

5. The vector of claim 4 wherein said vector is a plasmid based vector.

6. The vector of claim 4 wherein said vector is a viral based vector.

7. A microbial or plant host cell transformed or transfected with a vector according to claim 4.

8. A method for controlling plant cell proliferation comprising:
   introducing into said cell a genetic construct comprising a nucleotide sequence which encodes a regulatory protein characterized by the following:
      (a) is a Polycomb group member;
      (b) comprises a SET domain or a CXC domain or both;
      (c) regulates cell proliferation; and
said nucleotide sequence being capable of hybridizing under conditions of high stringency to SEQ ID NO:1, said nucleotide sequence being operably linked to promoter and regulatory regions capable of inducing expression in a plant cell.

9. The method of claim 8 wherein said cell proliferation is increased.

10. The method of claim 9 wherein said increased cell proliferation comprises endosperm cells.

11. An isolated nucleotide sequence which controls cell proliferation either positively or negatively comprising a nucleotide sequence which encodes upon expression a regulatory protein characterized by the following:
   (a) is a Polycomb group member;
   (b) comprises a SET domain or a CXC domain or both;
   (c) regulates cell proliferation; and
said nucleotide sequence being capable of hybridizing under conditions of high stringency to SEQ ID NO:3.

12. An isolated nucleotide sequence which controls cell proliferation either positively or negatively comprising a nucleotide sequence which encodes upon expression a regulatory protein comprising the following:
   (a) is a Polycomb group member;
   (b) comprises a SET domain or a CXC domain or both;
   (c) regulates cell proliferation; and
said nucleotide sequence being capable of hybridizing under conditions of high stringency to SEQ ID NO:4.

13. A method of regulating seed development in plants comprising:
   introducing to a plant cell a genetic construct comprising the nucleotide sequences of claims 1, 11 or 12.

14. The method of claim 13 wherein said construct is an expression construct.

15. The method of claim 14 wherein said regulation involves increasing endosperm content of a seed.

16. A seed produced by the method of claim 13.

17. A purified and isolated nucleotide sequence which encodes upon expression a regulatory protein comprising the following:
   (a) is a Polycomb group member;
   (b) comprises a SET domain or a CXC domain or both;
   (c) regulates cell proliferation; and said nucleotide sequence comprises SEQ ID NO: 1 or a region of at least 100 bases therefrom.

* * * * *